(12) United States Patent
Sterner et al.

(10) Patent No.: US 9,370,502 B2
(45) Date of Patent: Jun. 21, 2016

(54) PHARMACEUTICAL COMPOSITIONS CONTAINING OLIGOMERIC LACTIC ACID

(71) Applicant: LACCURE AB, Helsingborg (SE)

(72) Inventors: Olov Sterner, Malmö (SE); Sören Kulstad, Hörby (SE); Jeanette Robertsson, Malmö (SE); Malgorzata Sznitowska, Gdansk (PL); Werner Schubert, Askim (SE)

(73) Assignee: LACCURE AB, Helsingborg (SE)

( * ) Notice: Subject to any disclaimer, the term of this patent is extended or adjusted under 35 U.S.C. 154(b) by 0 days.

(21) Appl. No.: 14/414,745

(22) PCT Filed: Jul. 5, 2013

(86) PCT No.: PCT/EP2013/064265
§ 371 (c)(1),
(2) Date: Jan. 14, 2015

(87) PCT Pub. No.: WO2014/012805
PCT Pub. Date: Jan. 23, 2014

(65) Prior Publication Data
US 2015/0164848 A1    Jun. 18, 2015

(30) Foreign Application Priority Data
Jul. 16, 2012    (DK) .................................. 2012 70431

(51) Int. Cl.
| | | |
|---|---|---|
| *A01N 37/02* | (2006.01) |
| *A61K 31/225* | (2006.01) |
| *A61K 31/765* | (2006.01) |
| *C07C 69/68* | (2006.01) |
| *A61K 9/08* | (2006.01) |
| *A61K 47/38* | (2006.01) |
| *A61K 9/70* | (2006.01) |
| *A61K 9/00* | (2006.01) |

(52) U.S. Cl.
CPC ............. *A61K 31/225* (2013.01); *A61K 9/0034* (2013.01); *A61K 9/08* (2013.01); *A61K 9/7053* (2013.01); *A61K 9/7061* (2013.01); *A61K 9/7084* (2013.01); *A61K 31/765* (2013.01); *A61K 47/38* (2013.01); *C07C 69/68* (2013.01)

(58) Field of Classification Search
USPC .......................................... 514/547, 2.3, 2.4
See application file for complete search history.

(56) References Cited

U.S. PATENT DOCUMENTS

2011/0020265 A1 *    1/2011    Batcheller .............. A61K 31/19
                                                         424/78.37

FOREIGN PATENT DOCUMENTS

| WO | WO 03/016259 A2 | 2/2003 |
| WO | WO 2008/119518 A1 | 10/2008 |

OTHER PUBLICATIONS

Shin Etsu web page; http://www.metolose.jp/e/pharmaceutical/tc-5.shtml; Mar. 5, 2002.*
Schliecker et al., "Characterization of a homologous series of d,l-lactic acid oligomers; a mechanistic study on the degradation kinetics in vitro," Biomaterials, vol. 24, No. 21, pp. 3835-3844, Sep. 1, 2003.
International Search Report issued on Sep. 25, 2013 in application No. PCT/EP2013/064265.

* cited by examiner

*Primary Examiner* — Pancham Bakshi
(74) *Attorney, Agent, or Firm* — Foley & Lardner LLP

(57) ABSTRACT

A composition comprising i) oligomeric lactic acid with the following formula (I) wherein n is an integer from 2 to 20, from 2 to 19, or from 2 to 18, and wherein from about 10 to about 20% w/w of the total weight of the oligomeric lactic acid is a trimer, $HL_3$, having n equal to 2, wherein the number average molecular weight $M_n$ of the oligomeric lactic acid is from about 200 to about 500, and ii) a mucoadhesive agent.

20 Claims, 9 Drawing Sheets

Figure 1:
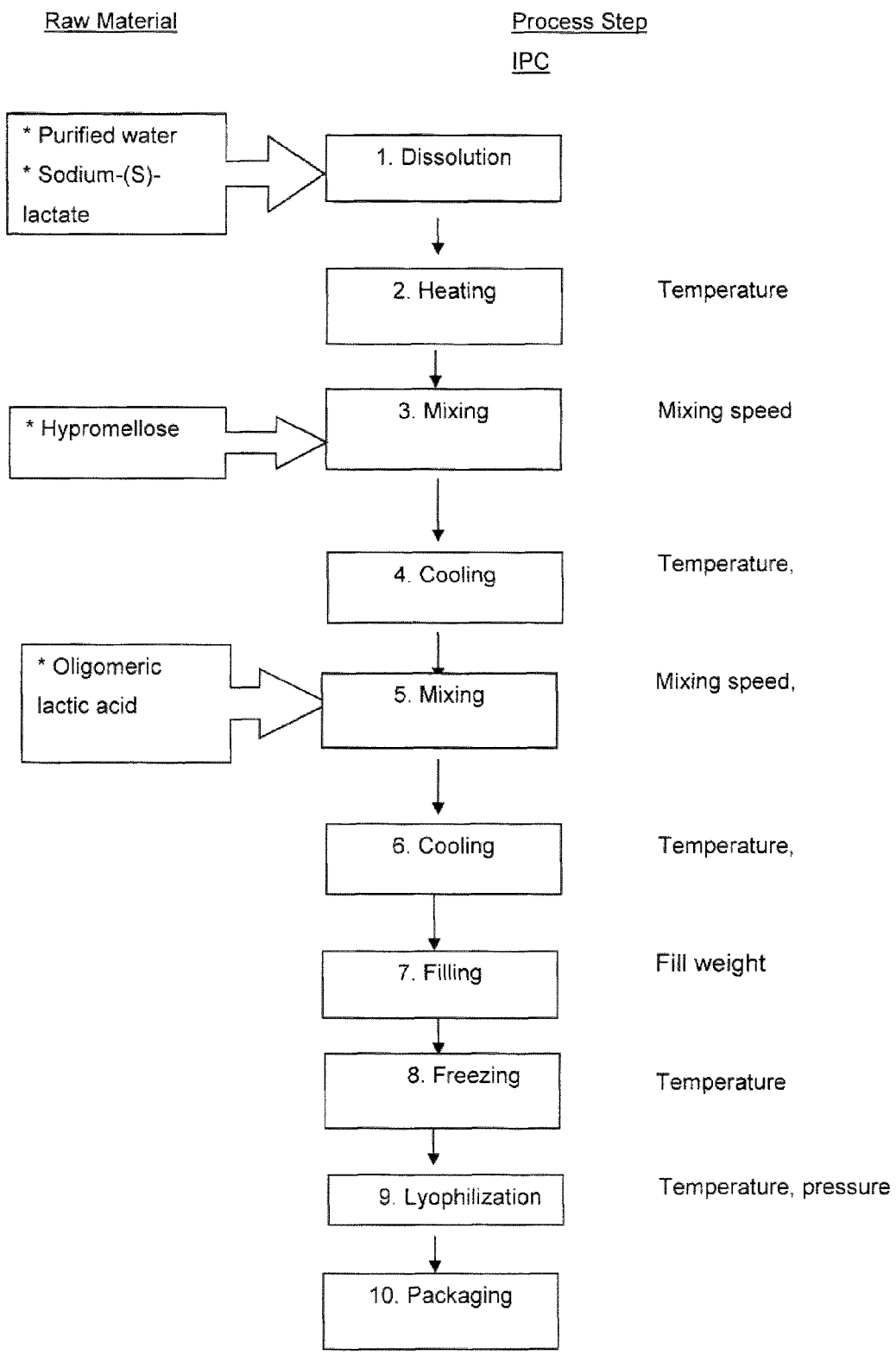

Figure 1 - Flow Chart of Manufacturing Process and Process Controls

Figure 2:
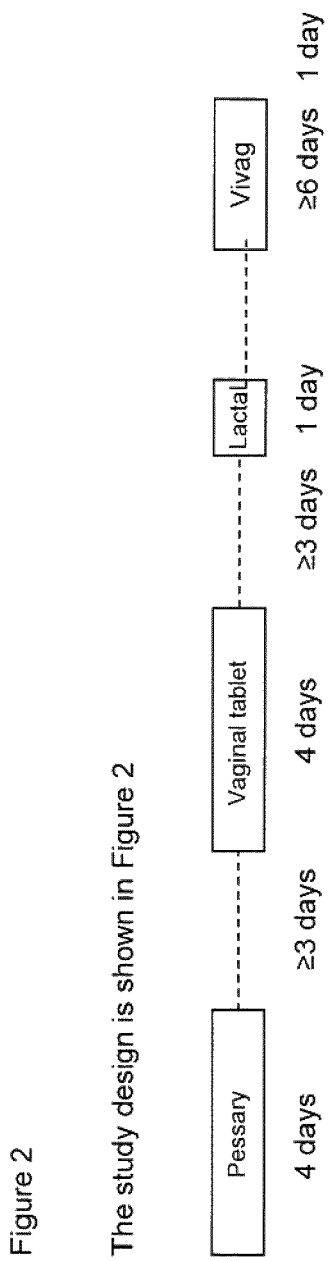

The study design is shown in Figure 2

PHARMACEUTICAL COMPOSITIONS CONTAINING OLIGOMERIC LACTIC ACID

FIELD OF THE INVENTION

The present invention relates to novel pharmaceutical composition comprising oligomers of lactic acid. The compositions are suitable for use in the treatment or prophylaxis of diseases or conditions where a local lowering of pH is desired to reach a pH between 3.8 and 5. Such diseases or conditions include bacterial, viral or fungal disease. Especially, the compositions are suitable for treating gynaecological diseases such as gynaecological infections. The compositions have proved to be useful for treating bacterial vaginosis. The compositions release the active ingredient, lactic acid, in a prolonged matter, which enables an administration frequency of once or twice a week to obtain the desired therapeutic effect.

BACKGROUND OF THE INVENTION

Gynaecological or reproductive tract infections generally refer to three different types of infection which affect the reproductive tract. Endogenous infections include bacterial vaginosis and candidosis, which result from an overgrowth of organisms which are normally present in the vagina. The endogenous infections represent the most common form of lower gynaecological tract infections (LGTIs) worldwide, and they can be easily treated. However, they commonly reappear, which is a major medical problem. Iatrogenic infections represent a second group which occur when the infectious agent (a bacterium or other micro-organism) is introduced into the reproductive tract through various routes such as menstrual regulation, induced abortion, IUD insertion or during parturition. Finally, sexually transmitted infections (STIs) are caused by microorganisms such as viruses, bacteria, or parasitic microorganisms that are transmitted through sexual activity with an infected partner. Among the STIs there are several serious diseases such as HIV, *chlamydia trachomatis*, condyloma accuminata, syphilis and *Neisseria gonorrhea*. STIs can affect both men and women, but a transmission from mothers to children during pregnancy and childbirth may also occur.

Bacterial vaginosis (BV) is the most frequent endogenous infection and also the most common medical condition of the female genital tract. BV is linked to increased complications in pregnancy, and may be involved in the pathogenesis of pelvic inflammatory disease and women's risk of acquiring HIV. Still many questions remain about its aetiology, which complicates the management of recurrent infections.

BV is an overgrowth of anaerobic bacteria and a lack of normal Lactobacilli flora, which results in an imbalance of normal vaginal flora. During pregnancy BV is associated with poor perinatal outcome and a cause of preterm birth. Identification and treatment of BV may reduce the risk of such consequences. A range of therapeutic options has been tested in order to manage or prevent recurrences of BV.

It is not yet known whether frequent episodes of BV are the result of re-infection or relapse. The association of BV with sexual behaviour suggests that BV is sexually transmitted and that additional episodes may be due to re-infection. However, evidence do not support the theory of sexual transmission and re-infection and several studies evaluating risk factors for repeated episodes of BV suggest it is due to relapse. Women developing early recurrence tend to complain of abnormal discharge at the end of therapy. Moreover, asymptomatic women who consider themselves cured after treatment, continued to have abnormal vaginal flora. Furthermore, the more severe the abnormality the earlier is usually the recurrence.

The value of bacteriotherapy, using harmless bacteria to displace pathogenic organisms remain unresolved.

Psychosexual symptoms with lack of libido and anxiety about infection may be reported by some women as a consequence of recurrent episodes of bacterial vaginosis and associated malodour. However, concurrent treatment of the male partner does not reduce the rate of BV relapse. However, condom use with male sexual partners may help to reduce the risk of relapse of bacterial vaginosis. Hormonal contraception use does not increase the incidence of bacterial vaginosis, while women with an intrauterine contraceptive device or system in situ may have an increased risk of BV.

Vaginal Discharge

Vaginal discharge is a common presenting symptom, which may be physiological or pathological. While BV remains one of the most common diagnoses in women attending genitourinary medicine clinics, vulvovaginal candidiasis is another common infective cause of vaginal discharge that affects about 75% of women at some time during their reproductive life. Approximately 50% of cases of bacterial vaginosis are asymptomatic and the true prevalence of this condition in the community is about 10-30%. Lactobacilli colonising the vaginal epithelium may have a role in defence against infection. Normal vaginal flora (lactobacilli) maintains the vaginal pH between 3.8 and 4.4. The quality and quantity of vaginal discharge may be altered in the same woman over time. There is a wide variation in vaginal discharge and each woman has her own sense of normality and what is acceptable or excessive.

The main problem of the pathogenic vaginal discharge is the malodour. This odour has the characteristics of a foul fishy smell which is characteristic for bacterial vaginosis and caused by amines, mainly trimethylamine. Other clinical manifestations may be excessive discharge and a sense of unfreshness.

The present invention is a further development of the invention disclosed in WO 2008/119518 published on 9 Oct. 2008. In WO 2008/119518 oligomers of lactic acid and their therapeutic and prophylactic use are described. However, the formulations described therein suffered from problems envisaged during initial clinical studies such as too early discharge etc. and, accordingly, there is still a need for developing compositions that are user-friendly and remain on the administration site for a period of time to that allow administration only once or twice weekly.

DETAILED DESCRIPTION OF THE INVENTION

As appears from the above there is a need for developing formulations that are suitable for use in management of gynaecological infections, notably bacterial vaginosis, and that enable a less frequent administration compared to the treatment regimens known today that requires daily or more than daily administration.

To this end, the present inventors have found that oligomers of lactic acids are suitable for use, cf. WO 2008/119518. On the one hand the oligomers release lactic acid once they are contacted with an aqueous medium and on the other hand the oligomers serve as a lactic acid depot, i.e. not all lactic acid is released immediately; the release of lactic acid is dependent on the oligomer in question.

However, the oligomers of lactic acid have different physical appearance dependent on the average molecular weight and the polydispersity index and, accordingly, some oligomers are easier to process into a composition for the manufacturer. The degree of polymerization, PDn, also plays a role.

It is also important to choose an oligomer of lactic acid that gives the desired effect for a desired period of time and at the same time provides the oligomer in a composition that is suitable for use by the end-user.

The present invention addresses these issues and preliminary clinical studies have been carried out to investigate whether the compositions of the oligomeric lactic acid provide the desired effects.

Various compositions are mentioned in WO 2008/119518. However, the present inventors have found that in order to achieve the desired prolonged effect that enables administration once a week, the oligomeric lactic acid must have a broader molecular weight distribution, i.e. a polydispersity index that is greater than envisaged in WO 2008/119518. Moreover, the degree of polymerization, PDn, must not be higher than 4.1. The present inventors have also found that it is important to select an oligomeric lactic acid that has a physical appearance that is somewhere between a semi-solid and a solid and somewhere between sticky and smooth. This is important in order to process the oligomeric lactic acid into a composition that is suitable for use. It is envisaged that the number average molecular weight as well as the polydispersity index are important parameters to obtain the desired duration of therapeutic effect as well as a physical appearance that facilitates or enables manufacturing of a pharmaceutical composition.

As discussed herein, Amsel's criteria are used in the diagnosis of BV and also as means for evaluating the effect of a certain treatment of BV. Amsel's criteria are
i) homogeneous discharge (thin, white, yellow),
ii) presence of clue cells,
iii) release of a fishy odour with application of potassium hydroxide to the discharge,
iv) pH above 4.5.

If three of the four criteria are fulfilled, the patient has BV.

However, the present inventors have found that the pH in the vagina after or during treatment (together with the other criteria mentioned above) is not decisive in evaluating whether the treatment was successful. The most important parameter seems to be that a certain decrease in pH takes place, not the actual value of pH. Thus, as seem from the clinical studies reported herein it seems as if a decrease of pH with 0.5 units or more is observed and only one or less of the other Amsel's criteria are not fulfilled, then the treatment has been effective.

Accordingly, in order to evaluate a treatment of BV the following should be tested:
i) homogeneous discharge (thin, white, yellow),
ii) presence of clue cells,
iii) release of a fishy odour with application of potassium hydroxide to the discharge,
iv) ΔpH of less than 0.5 (i.e. not including 0.5), where ΔpH is the difference in pH in vagina before treatment and after treatment.

If three of the four criteria are fulfilled, the treatment has not been effective against BV.

The aim of the present invention is to provide a composition comprising an oligomeric lactic acid in a form that is easy to handle and insert in the vagina by the end-user and wherein the duration of the effect is so long that administration once, or once monthly (for prevention of recurrence) is sufficient (although there may be situations where administration more than once and more than once weekly such as twice weekly may be required). Moreover, it is an aim to provide a composition that is easy to manufacture and in a reproducible manner fulfils the generally applicable requirements with respect to variation in mass variation, disintegration, dissolution, stability etc.

The mode of action of the oligomeric lactic acid in the compositions of the present invention is to gradually release lactic acid, which in turn ensures a weak acidic environment on the administration site. In principle this means that such compositions can be used for the treatment of any disease or condition, which would benefit from establishing a weak acid environment. Examples are
i) gynaecological infections,
ii) oral mucosal lesions due to bacterial, viral or fungal infections or other medical reasons like e.g. leucoplacia or "Burning Mouth Syndrome",
iii) rectal diseases or disorders such as haemorroids, anal fissures, pruritus ani or proctitis,
iv) skin diseases or disorders such as wounds, exema, atopic dermatitis, psoriasis, acne, rosacea, urticaria, pruritus, light dermatosis, hyperhidrosis, alopecia, as well as bacterial infections, viral infections, fungal infections, and ectoparasites,
v) treatment or prophylaxis of caries and/or parodontitis and/or halitosis, or
vi) in gastroenterology, where beneficial effects may be seen in acid disorders such as achylia.

The compositions of the present inventions are especially suitable for use in the prophylaxis and/or treatment of gynaecological infections. The gynaecological infection may be a bacterial infection, such as bacterial vaginosis, unspecific colpitis, senile colpitis, cervicitis, and urethritis. It can also be a fungal infection, such as candidosis (*candida albicans*), cryptococcosis, actinomycosis, or a viral infection, such as Human Immunodefiency Virus (HIV), Herpes Simplex Virus (HSV), Human Papilloma Virus (HPV).

Release of lactic acid is as follows:

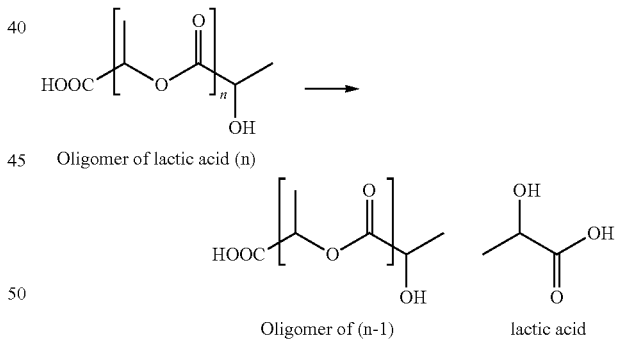

Bacterial Vaginosis (BV); its Background and Epidemiology

BV is characterised by a malodorous vaginal discharge, a vaginal pH of more than 4.5, a positive amine test, and a thin homogeneous white fluor, and the presence of clue cells microscopically and on occasion vaginal burning or itching.

The vaginal flora is altered from the normal lactobacilli (LB) dominant to flora with reduced numbers of LB and an overgrowth of *Gardnerella vaginalis, Mycoplasma hominis*, and anaerobic bacteria such as streptococci, *Prevotella* spp, and *Mobiluncus* spp.

Bacterial vaginosis is commonly diagnosed by Amsel's criteria if 3 of the following 4 criteria are present: 1; a vaginal pH higher then 4.5, 2; the presence of clue (vaginal epithelial) cells in the vaginal fluid, 3; a thin grey or white homogenous discharge, 4; or a positive KOH "whiff" test (release of fishy odour upon the addition of 10% potassium hydroxide to the vaginal fluid)

Some predisposing factors have been shown to increase the risk of BV, such as younger age, black ethnicity, douching, smoking, and the IUD contraception. Several reports have linked BV with sexual behaviour, a recent change of sexual partner, as well as multiple partners.

Management of Bacterial Vaginosis

When using oral or vaginal preparations of metronidazole and clindamycin, women will have an initial 80-90% response to treatment but there will be 15-30% relapse within 3 months. When considering the association between lactobacilli, hydrogen peroxide production, vaginal pH, and overgrowth of BV associated bacteria, adjustment of only one of these may help some women with recurrent BV, but it may be insufficient to resolve all cases.

Although there is a well-known inter-relation between lactobacilli, hydrogen peroxide production, vaginal pH, and overgrowth of BV associated bacteria, the initiating factor for BV remains unresolved.

Treatment only focusing on one aspect of this inter-relation may benefit some women with recurrent BV, but a combined approach is superior. Since bacterial vaginosis can also be asymptomatic, recurrence often cannot be differentiated from treatment failure. Thus, recurrent bacterial vaginosis may be prevented by using effective therapy for the initial episode.

Acidifying Properties

A low pH of the vagina is due to production of lactic acid by lactobacilli metabolism, and as well as the conversion of glycogen to lactic acid by oestrogenised vaginal epithelial cells. In culture lactobacilli acidify their growth medium to a pH of 3.2-4.8. At that pH range a steady state of equilibrium develops where the acidity becomes auto-inhibitory. Anaerobes grow poorly at pH 4.5 or less. In vitro studies show that the concentrations of BV associated bacteria increase with increasing vaginal pH. However, it has been found that lactic acid and low pH caused more mashed inhibitory effect of these bacteria than hydrogen peroxide. However, when there is a rise in vaginal pH, such as after sex and during menses, bacterial overgrowth could occur. Interestingly, a low pH seems to be important for adherence of lactobacilli to the epithelial cells. BV can also be induced by inoculating BV associated bacteria into a healthy vagina as shown in the initial work by Gardner and Dukes (Gardner H L, Dukes C D. *Haemophilus vaginalis* vaginitis. Am J Obstet Gynecol 1955; 69:962-76).

Thus, the exact mechanism for the onset of BV remains unsolved. BV is associated with a reduced number of lactobacilli (LB) and a lower hydrogen peroxide production. There is a rise in the vaginal pH, and the overgrowth of BV associated organisms. Currently, it is not known what causes the reduction in hydrogen peroxide producing strains of lactobacilli in BV.

In other words, up to now it has generally been recognized that the main goal to prevent or treat BV is to keep the vaginal pH at 4.5 or less. This will prevent overgrowth of pathogenic bacteria until the normal LB are re-established and able to maintain the pH. However, as seen from the examples herein an important factor in the management of BV is to lower the pH from the initial value, but the results also demonstrate that it is not so important to reach a pH of 4.5 or less; the most prominent effect is a lowering of pH as such. It has been demonstrated in the examples that a decrease in pH from the original value with 0.5 pH-units or more (such as 1.0) is an indication of an effective treatment. Thus, revised criteria for evaluating a specific treatment of BV after one treatment course could be:

i) homogeneous discharge (thin, white, yellow),
ii) presence of clue cells,
iii) release of a fishy odour with application of potassium hydroxide to the discharge,
iv) a decrease in vaginal pH of less than 0.5 pH-units measured 3 or 4 days after the treatment,
where at least 3 out of 4 criteria should be fulfilled, if the patient still suffers from BV, i.e. indicating that the treatment was not effective.

Intermittent pH lowering therapy, on an episodic or prophylactic basis, may be considered to prevent recurrent BV.

Compositions Comprising Oligomeric Lactic Acid

The invention relates to compositions comprising oligomeric lactic acid, method for preparing such compositions as well as the use of such compositions for the treatment or prophylaxis of conditions, where a local lowering of pH is desired. The pH should be lowered to a pH value in a range of from about 3.5 to about 5. Such conditions are described above and include the prophylaxis and/or treatment of bacterial vaginosis.

As mentioned above the present invention is a further development of the findings reported in WO 2008/119518. Although many oligomeric lactic acids and compositions containing them are described, the present inventors have found that there still is a need for selecting the oligomeric lactic acid that has the most suitable properties for i) being processed into a pharmaceutical composition, ii) having the desired effect, iii) having the desired duration of action, and iv) being convenient for the patient to administer. Moreover, as the primary aim is to develop a composition that remains on the administration site for a desired period of time, the present inventors were also faced with technical problems relating to how to obtain a suitable mucoadhesiveness of the final composition.

These problems have been solved by providing a composition comprising
i) oligomeric lactic acid with the following formula

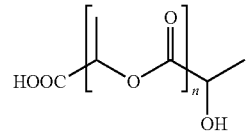

wherein n is an integer from 2 to 20, from 2 to 19, or from 2 to 18, and wherein from about 10 to about 20% w/w of the total weight of the oligomeric lactic acid is a trimer, $HL_3$, having n equal to 2, and
ii) a mucoadhesive agent.

As seen from the examples herein—and in contrast to what was envisaged in WO 2008/119518—the present inventors have found that the oligomeric lactic acid must have properties in order to achieve a duration of action that is sufficient to avoid more than one or two administration(s) (unless recurrence is an issue, as discussed herein). Thus, the number average molecular weight should be in a range of from about 200 to about 500, the degree of polymerization PDn should be at the most 4.1 and the molecular weight distribution should not be too narrow, i.e. a specific oligomeric acid contains a range of oligomers with n in a range of from 1 to 13. The polydispersity index should be 1.45 or more.

In particular, the number average molecular weight should be in a range of from about 200 to about 240, the weight average molecular weight should be in a range of from about 290 to about 500, the polydispersity index should be in a range of from 1.45 to 2.5. Normally, the degree of polymerisation should be from 2.5 to 3.8.

The number average molecular weight may also be in a range of from about 255 to about 425, the weight average molecular weight is then in a range of from about 370 to 580, the polydispersity index in a range of from 1.45 to 2.5. Normally, the degree of polymerization should be from 3 to 4.1.

Moreover, as mentioned above, the oligomeric lactic acids have different physical appearance dependent on the average molecular weight and the polydispersity. The physical appearance may be from a liquid (low average molecular weight) over semi-solid to a solid form (higher average molecular weight). Some of the oligomeric lactic acids have adhesive properties that are sufficient to impart the necessary mucoadhesiveness to a composition. However, even if the selected oligomeric lactic acids have some mucoadhesiveness, the present inventors have found that combining the oligomeric lactic acids with a mucoadhesive agent is necessary in order to ensure that the composition remains on the administration site for a desired period of time.

The number average molecular weight $M_n$ of the oligomeric lactic acid is from about 200 to about 500. As seen from the examples herein suitable results have been obtained with oligomeric lactic acid having a number average molecular weight from about 200 to about 350, As mentioned above, the polydispersity index is also important to ensure a relatively rapid onset of action as well as a prolonged effect. Without being bound to any theory it is believed that the low molecular weight oligomeric acids contained in oligomeric lactic acid included in the composition are responsible for the rapid onset of action as well as short-medium duration, whereas the "high" molecular weight oligomeric acids contained in oligomeric lactic acid included in the composition are responsible for the longer duration.

Thus, a composition of the present invention contains an oligomeric lactic acid which has a polydispersity index from about 1.45 to about 6. As seen from the examples herein suitable results have been obtained when the degree of polymerization (PDn) of the oligomeric acid is from about 2.5 to about 4.1, in particular when the oligomeric acid has a degree of polymerization of from 3 to 3.6.

As demonstrated in the examples herein a composition according to the present invention contains an oligomeric lactic acid, which comprises:
from 10 to 20% w/w of $HL_2$ (i.e. n=1)
from 10 to 20% w/w of $HL_4$ (i.e. n=3)
from 10 to 15% w/w of $HL_5$ (i.e. n=4)
from 5 to 15% w/w of $HL_6$ (i.e. n=5).

The oligomeric lactic acid may also comprise from 1% to 5% w/w of each of $HL_{10}$, and $HL_{11}$; $HL_{10}$, $HL_{11}$, and $HL_{12}$; $HL_{10}$, $HL_{11}$, $HL_{12}$, and $HL_{13}$; $HL_{10}$, $HL_{11}$, $HL_{12}$, $HL_{13}$, and $HL_{14}$.

Of particular interest is a composition, wherein the oligomeric lactic acid is OMLA 3, 6 or OMLA 22 having the following constitution:
from 7 to 10% of $HL_1$,
from 12 to 15% w/w of $HL_2$ (i.e. n=1)
from 14 to 16% w/w of $HL_3$ (i.e. n=2)
from 11 to 15% w/w of $HL_4$ (i.e. n=3)
from 10 to 14% w/w of $HL_5$ (i.e. n=4)
from 8 to 10% w/w of $HL_6$ (i.e. n=5), and
the decreasing weight percentage of $HL_7$-$HL_{18}$.

Figure 3:
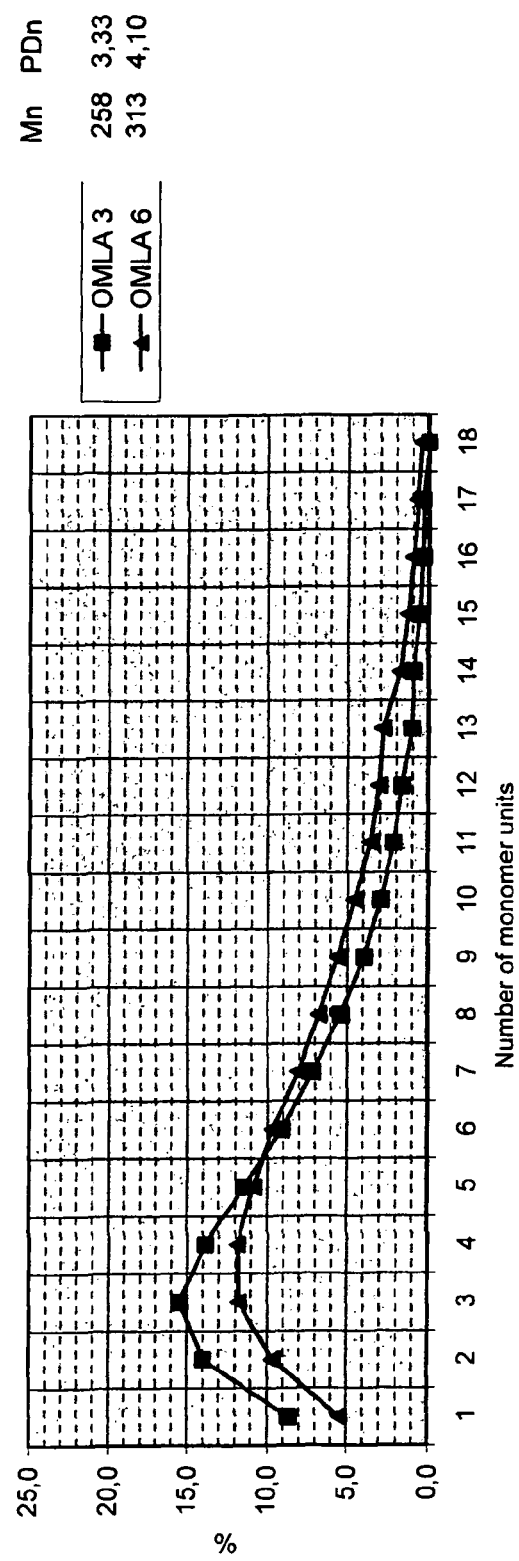
Figure 5:
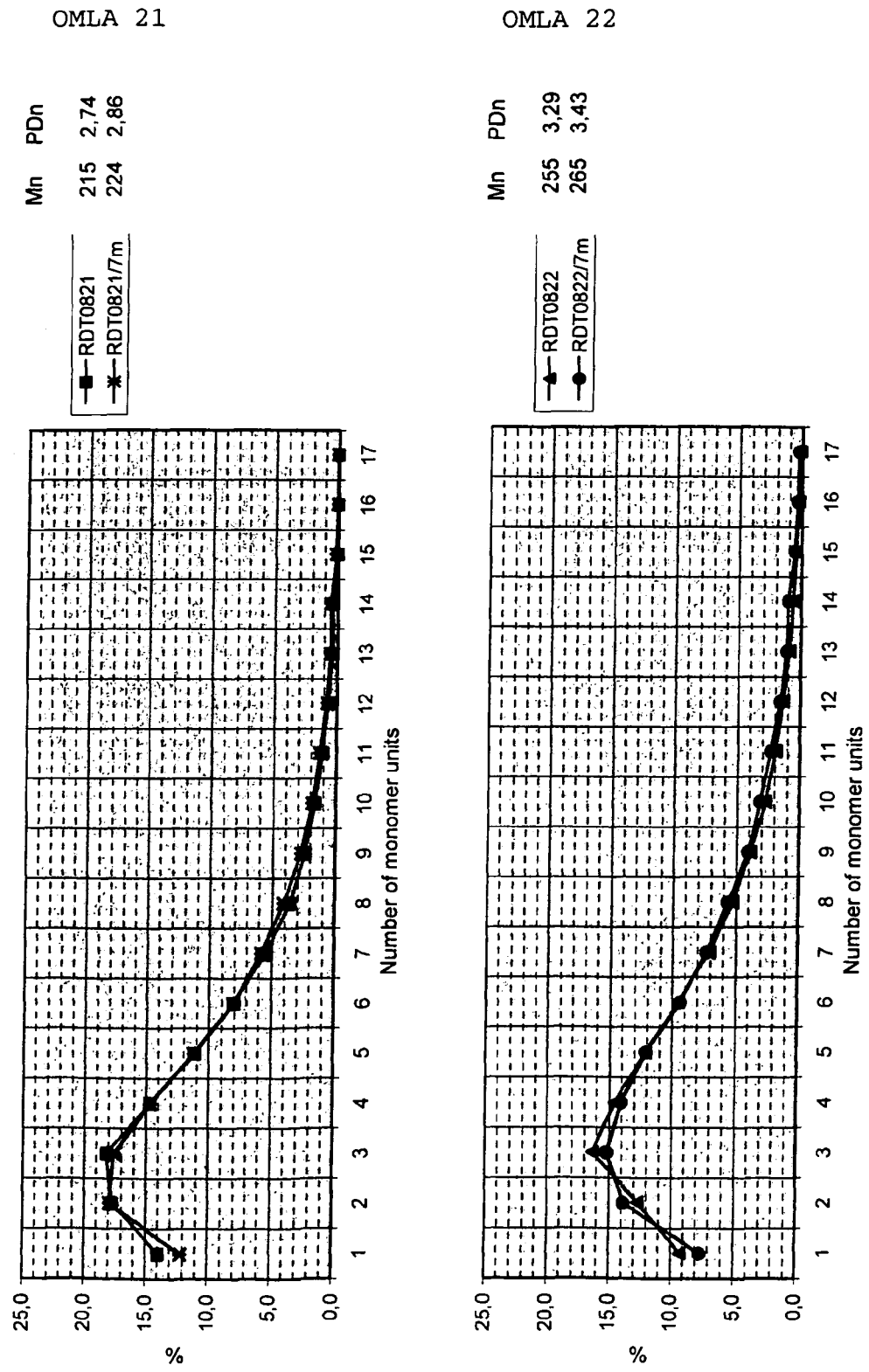

This oligomeric lactic acid is also described in detail in FIG. 3 (OMLA 3 and OMLA 6) and FIG. 5 (OMLA 22) herein, where the number average molecular weight and the degree of polymerization is given (OMLA 3: Mn is 258, PI is 1.48 and PDn is 3.33; OMLA 6: Mn 313, PI is 1.50 and PDn 4.1; and OMLA 22: Mn 255 and PDn 3.29 or Mn 265, PI is 1.46 and PDn 3.43).

As mentioned above an important agent in a composition according to the invention is a mucoadhesive agent. The combined effect of mucoadhesiveness of the oligomeric lactic acid and the mucoadhesive agent make it possible to obtain a composition that after administration to the administration site (e.g. into the vagina) utilizes the relatively small amount of body fluid present at the administration site to become mucoadhesive and to adhere to the mucosa for a period of time that results in sufficient treatment.

Mucoadhesion (or bioadhesion) is defined as the process whereby synthetic and natural macromolecules adhere to various mucosal surfaces in the body. If a molecule possesses mucoadhesive properties or if such mucoadhesive materials are incorporated as constituents into pharmaceutical formulations or compositions, local drug action or drug absorption by mucosal cells may be enhanced or prolonged. Moreover, if mucoadhesive properties are present in the molecule or if mucoadhesive constituents are incorporated, drug release and action may be increased at the site of application for an extended period of time. It is also important that the composition stays on the administration site for as long as desired.

The mucoadhesive agent may be a cellulose derivative selected from hydroxypropyl methylcellulose (HPMC), methyl cellulose, hydroxyethyl cellulose (HEC), hydroxypropyl cellulose (HPC), ethyl hydroxyethyl cellulose, carboxymethyl cellulose, carboxymethyl cellulose including sodium carboxymethyl cellulose, and microcrystalline cellulose, and mixtures thereof.

Specific cellulose derivatives are:
Hydroxypropylmethylcelluloses (HPMC):
Metolose-60-SH-15, Metolose-60-SH-50, Metolose-60-SH-10000, Metolose-65-SH-50, Metolose-65-SH-400, Metolose-65-SH-1500, Metolose-90-SH-400, Metolose-90-SH-4000, Metolose-90-SH-15000, Metolose-90-SH-100000, Pharmacoat 606, Shin-Etsu, Tokyo, Japan; however, as discussed below HPMC with a viscosity in a range of from 10 to 20 cP are preferred.
Methylcelluloses (MC):
Metolose SM-4 (MC1), Metolose SM-15 (MC2), Metolose SM-100 (MC3), Metolose SM-400 (MC4), Metolose SM-1500 (MC5), Metolose SM-4000 (MC6), Shin-Etsu; the first three methylcelluloses mentioned are preferred.
Sodium Crosscarmelose (CMC):
Low viscosity CMC (CMC1), Medium viscosity CMC (CMC2), High viscosity CMC (CMC3), Sigma-Aldrich, St. Louis, USA
Hydroxyethylcellulose (HEC):
Natrosol 250 HX, Hercules, Wilmington, USA.

The mucoadhesive agent may be
a starch derivative including moderately cross-linked starch;
an acrylic polymer;
a carbomer and its derivatives (Polycarbophyl, Carbopol®, etc);
a chitosan (poly-(D-glucosamine);
a natural polymer including gelatin, sodium alginate, pectin, scleroglucan, tragacanth, gellan, xanthan gum or guar gum;
a poly co-(methylvinyl ether/maleic anhydride), and
mixtures thereof and mixtures thereof with one or more of the cellulose derivatives mentioned above.

As seen from the examples herein suitable results are obtained when the mucoadhesive agent is hydroxypropyl methylcellulose.

Hydroxypropyl methylcellulose (HPMC) is also denoted hypromellose (USP) or hypromellosum (Ph. Eur.). The chemical name is cellulose, 2-hydroxyropyl methyl ether (CAS 9004-65-3). Dependent on the substitution pattern HPMC is also divided into different types:

| Type | Methoxy content JP 2001 | Methoxy content USP 25 | Hydroxy-propoxy content JP 2001 | Hydroxy-propoxy content USP 25 |
|---|---|---|---|---|
| Type 1828 | | 16.5-20.0% | | 23.0-32.0% |
| Type 2208 | 19.0-24.0% | 19.0-24.0% | 4.0-12.0% | 4.0-12.0% |
| Type 2906 | 27.0-30.0% | 27.0-30.0% | 4.0-7.5% | 4.0-7.5% |
| Type 2910 | 28.0-30.0% | 28.0-30.0% | 7.0-12.0% | 7.0-12.0% |

Moreover, the individual types are available in many different viscosity types (see e.g. Handbook of Pharmaceutical Excipients, 4$^{th}$ Edition, PhP Press, 2003). Thus, Type 2910 is available in qualities having a viscosity ranging from 3 to 15 cP (e.g. available from ShinEtsu from Japan), more specifically in the following viscosities: 3, 4.5, 6 and 15 cP. The viscosity is the apparent viscosity. More details regarding measuring the viscosity of HPMC is given in Handbook of Pharmaceutical Excipients, 4$^{th}$ Edition, PhP Press, 2003, i.e. measuring a 2% w/v aqueous solution at 20° C.

An interesting result reported in the examples herein is where type 2910 with a viscosity of 15 cP has been employed. A person skilled in the art can based on the examples given herein perform the necessary adjustments in order to use other combinations of mucoadhesive agents, notably HPMC, and oligomeric lactic acid, especially in view of the results given herein.

Thus, a composition of the invention may contain HPMC as mucoadhesive agent, wherein the viscosity of the hydroxypropyl methylcellulose is from about 10 to about 20 cP.

The concentration of the mucoadhesive agent in the composition may be in the range from 10 to 65% w/w, from 20 to 60% w/w, from 30 to 50% w/w or from 35 to 45% w/w. In a particularly interesting example, the concentration of the mucoadhesive agent in the composition is 39-42% w/w (Example 9).

When hydroxypropyl methylcellulose is employed it is normally in the range from 5 to 65% w/w, from 20 to 60% w/w, from 30 to 50% w/w or from 35 to 45% w/w.

As demonstrated in the examples herein suitable pH lowering effect has been obtained in clinical studies using a composition of the present invention. Moreover, the composition has remained on the administration site (it did not fall out or was discharged). The clinical studies moreover confirm that women suffering from BV are effectively treated with a composition of the invention only after one treatment, i.e. only one administration. In some cases, the administration may be once or twice during a week, normally only once. In those cases where recurrence is envisaged it is recommended to repeat the treatment once monthly.

A composition according to the invention may also contain one or more one or more pharmaceutically acceptable excipients.

The pharmaceutically acceptable excipients may be selected from the group consisting of carriers, diluents, binders, disintegrating agents, flow-improving agents, pH-adjusting agents, stabilising agents, viscosity adjusting agents, preservatives, gelling or swelling agents, surfactants, emulsifying agents, suspending agents, bases for suppositories, vagitories or pessaries, bases for creams, ointments, gels, lotions, shampoos, foam, sprays and the like. The specific choice of pharmaceutically acceptable excipients depends on the specific form or the formulation, e.g. the dosage form. A person skilled in the art can find guidance e.g. in Remington's Pharmaceutical Sciences (Gennaro, Alfonso R., ed., 18. ed., 1990, xvi, Mack, ISBN: 0-912734-04-3).

The final formulation may also comprise one or several pharmaceutically acceptable salts such as lactate, phosphate, succinate, lysinate, acetate, cypionate, valerate, hemisuccinate, butyrate, or trometamole salt alone or in combination. The amount of oligomeric lactic acid included in each dose preparation may range from 0.01 mg to 50 g per dose unit, but is preferentially 0.5 mg to 5 g. As seen from the examples herein a suitable dose is from about 250 mg to about 1 g such as 600 mg. The whole dose is normally contained in the composition. The composition of the invention may restore normal physiological pH in the vagina, although—as discussed herein before—the important feature is to reduce pH and it is not necessary in order for the composition to be effective to restore normal physiological pH. The decrease of pH will reduce the number of anaerobic bacteria which cause the characteristic unpleasant vaginosis malodour through trimethylamine production.

The composition comprises at least 5% w/w of the oligomeric lactic acid. As seen from the examples herein, the content of oligomeric lactic acid is normally in the range of from 20 to 80% w/w, notably from 20 to 50% w/w. In some examples the concentration in the final composition is from 30 to 45% w/w. In a particularly interesting example, the concentration of oligomeric lactic acid in the composition is 35-36% w/w (Example 9).

The content of oligomeric lactic acid in a composition of the invention corresponds to about 200-2000 mg of lactic acid, notably from 500 to 1000 mg of lactic acid. In a particularly interesting example, the content of oligomeric lactic acid corresponds to 700 mg lactic acid (Example 9).

In one embodiment the one or more oligomers of lactic acid release lactic acid over a time period of at least 8 hours, at least 12 hours, such as at least 16 hours, at least 20 hours, at least 24 hours, at least 36 hours, at least 2 days, at least 3 days, at least 4 days, at least 5 days, at least 6 days, or at least 7 days when exposed to water at room temperature.

In those cases where the composition is intended for gynaecological use, the composition is designed for vaginal administration including intravaginal or transvaginal administration.

The composition may be in solid, semi-solid or liquid form dependent on its use.

The specific form should be chosen dependent on the specific administration route. Thus, for oral administration (to the GI tract), semi-solid or solid compositions are preferred such as, e.g., solid dosage forms (e.g. tablets, capsules, sachets), powders, granules, beads, pellets etc. For topical administration or administration to the oral cavity gel, creams, ointments, lotions, powders, patches, tooth paste, mouth wash etc. may be suitable. A person skilled in the art will find guidance e.g. in Remington's Pharmaceutical Sciences for the preparation of such forms and for selection of suitable pharmaceutically acceptable excipients.

In a specific aspect the composition is designed to be administered to the vagina. In such cases the following dosage forms are suitable: a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, vaginal device, semipermeable packaging and any combination thereof. As seen from the examples herein a suitable composition is in the form of a vaginal tablet.

A vaginal tablet of the invention may comprise buffering or pH-adjusting agents, fillers, binders, lyophilisation aids or other pharmaceutically acceptable excipients normally employed for the preparation of tablet and/or for process steps involving a lyophilisation step.

Suitable buffering or pH-adjusting agents may be pharmaceutically acceptable buffering agents suitable for adjustment of pH to from about 3 to about 5.

Suitable agents include lactate (e.g. sodium lactate), acetate, citrate, malonate, phosphate, tartaric acid, maleate etc. As seen from the examples herein, lactate is preferred as a buffering or pH-adjusting agent; in this manner the agent is identical to the monomers of oligomeric lactic acid, which offers an advantage in that the buffer pair is lactic acid/oligomeric lactic acid/lactate.

The buffer of pH-adjusting agent provides a pH lower than about 5, such as lower than 4 in order to obtain a more rapid restoration of the acid milieu to optimize the therapeutic response and the regrowth of Lactobacilli. The lowering pH effect of the buffer depends on the pH value in at the application site, when the composition is administered.

As it appears from the examples herein, lactose is a suitable excipient. Lactose is filler or a lyophilisation aid, but the invention is not limited to the use of lactose as a person skilled in the art will know how to substitute lactose with other excipients. Suitable other excipients are e.g. maltose and trehalose. The concentration of lactose or an equivalent substance is normally in a range of from 5 to 35% w/w. In particular, the concentration is in a range from 5 to 20% w/w or from 5 to 15% w/w in a composition of the invention. As seen from example 9 herein the concentration is about 9-10% w/w. Other dissacharides like e.g. sucrose, lactulose, cellobiose etc. may also be suitable for use in the present context. In a composition of the invention, a dissacharide normally contribute to a suitable structure of the composition.

An oligomeric lactic acid may be incorporated into a device as a controlled release drug delivery system.

The composition may comprise glycogen or precursors or derivatives thereof, e.g. to serve as a source of sustenance for *Lactobacillus*.

The composition may comprise probiotics in the form of live micro-organisms such as *Lactobacillus acidophilus* or similar species, which when administered in adequate amounts confer a health benefit on the host, resulting in a Lactobacilli-reestablishment of the *Lactobacillus*-dominant vaginal flora.

The pharmaceutically acceptable excipient may be a lipophilic or hydrophilic carrier. Examples of lipophilic carriers are waxes, oils, isopropyl myristate, solid triglycerides, and cocoa butter. Examples of hydrophilic carriers are glycerol, propylene glycol, polyoxyethylene glycol.

Pathogen-Antiadhesion Agents

The composition may further comprise one or more pathogen-antiadhesion agents. Lactobacilli which confer the favourable acidifying properties in the vaginal milieu are not adhered to the vaginal mucosa. However, pathogenic fungi are adhered to the mucosa and pathogenic bacteria may be in contact with the mucosa and degrade the protective lining of the normal healthy vaginal mucosa. This may enhance the risk of recurrence of the vaginosis in susceptible patients. Thus, a formulation includes one or several compounds that prevent such mucoadhesion by pathogens may be beneficial for the prophylaxis, prevention and treatment of bacterial vaginosis. The current invention may include one or several carrier core material which prevents the mucoadhesion of pathogenic microorganisms, preferentially anaerobic bacteria and fungi. Antiadhesion agents may be agents that serve as either a barrier preventing adhesion or as an agent that causes already adhered microorganisms to disadhere. Examples of antiadhesion agents causing disadherence may be mannose, lactose, xylitol, and other sugar alcohols.

The pathogen-antiadhesion agent may be selected from the group consisting of mannose, lactose, xylitol, and other sugar alcohols. As mentioned herein, lactose may also serve other purposes, but if present only as an anti-adhesion agent the concentration may be in the same range as other pathogen-antiadhesion agents, namely in the range 0.01 to 20% w/w of the final composition.

Antimicrobial Properties

A microbiological study throughout the menstrual cycle, has shown that the concentration of non-LB species was higher at menses. Thus, there is a potential for bacterial overgrowth at that time, since there is instability of the vaginal flora.

The idea of adding or including antibacterial components to the composition is that pathogenic bacteria produce hydrolytic enzymes which degrade the vaginal mucine lining. This effect of the pathogens damages the normal protective vaginal mucous lining.

The composition may also include one or more antimicrobial agents such as antibiotics, such as clindamycin or metronidazol, essential oils, such as tea tree oil, cations or elements, such as Hg, Cu, Pb, or Ag, polyene antimycotic, imidazole, triazole, allyamines, echinocandin, aciclovir, amantadine, alcohols, quartenary ammmonium compounds, boric acid, chlorhexidine gluconate, hydrogen peroxide, urea hydrogen peroxide, iodine, mercurochrome, octenine dihydrochloride, phenolic (carbolic acid) compounds, sodium chloride, sodium hypochlorite, nonoxynol as well as combinations and/or mixtures of such agents. An oxygenating compound such as $H_2O_2$ will provide an unfavourable milieu for the pathogenic anaerobic bacteria characteristic of the bacterial vaginosis. In addition, some oxygenating compounds such as $H_2O_2$ may also add antibacterial properties for the pathogens. Lactobacilli, which themselves produce $H_2O_2$, are less adversely affected of e.g. $H_2O_2$.

The antimicrobial agent may be used in appropriate concentrations recognised by a person skilled in the art. The concentration of antimicrobial agent may be more than 0.01 weight percent, such as is in the range 0.01 to 50 weight percent, such as 0.01 to 25 weight percent, from 0.05 to 25 weight percent, 0.1 to 10 weight percent, 0.5 to 5 weight percent of the composition.

A composition of the invention may further comprise an antibacterial agent selected from the group consisting of clindamycin, tetracycline, amoxicillin, ampicillin, erythromycin, doxycycline, lumefloxacin, norfloxacin, afloxam, ciproflaxin, azitromycin, cefltoxine, and chlorchinaldol.

A composition of the invention may comprise one or more antibacterial agents for the prophylaxis and/or treatment of gynaecological infections as defined herein. The antibacterial agent may be selected from the group consisting of clindamycin, tetracycline, amoxicillin, ampicillin, erythromycin, doxycycline, lumefloxacin, norfloxacin, afloxam, ciproflaxin, azitromycin, cefltoxine.

The amount of antibacterial agent may be in the range from 5 mg to 1000 mg per dose.

The antibacterial agent may also be selected from the group consisting of tetracycline, doxycycline, azithromycin, or erythromycin, or one or more broad spectrum antibiotic agent.

The broad spectrum antibiotic agent may be selected from the group consisting of clindamycin, tetracycline, amoxicillin, ampicillin, erythromycin, doxycycline, lumefloxacin, norfloxacin, afloxam, ciproflaxin, azithromycin cefltoxine for the prophylaxis and/or treatment of gonorrhea or chlamydial infections. In yet a further embodiment according to the invention the amount of broad spectrum antibiotic agent is in the range from 100 mg to 3000 mg per dose.

The broad spectrum antibiotic agent may also be selected from the group consisting of tetracycline, amoxicillin, ampicillin, lumefloxacin, norfloxacin, afloxam, ciproflaxin, azithromycin or cefltoxine for prophylaxis and/or treatment of gonorrhea. In a further embodiment according to the invention the amount of broad spectrum antibiotic agent is in the range from 400 mg to 3000 mg per dose, or the broad spectrum antibiotic agent may be selected from the group consisting of tetracycline, doxycycline, and erythromycin for treatment of chlamydial infections. In yet a further embodiment the amount of broad spectrum antibiotic agent is in the range from 100 mg to 2000 mg per dose. In yet a further embodiment the formulation is in the form of a tampon.

The composition may also comprise an antichlamydial agent selected from the group consisting of tetracycline, doxycycline, and erythromycin.

The composition may further comprise an antifungal agent selected from the group consisting of miconazole, terconazole, isoconazole, fenticonazole, fluconazole, nystatin, ketoconazole, clotrimazole, butoconazole, econazole, tioconazole, itraconazole, 5-fluoracil, and metronidazole. In another embodiment the amount of antifungal agent per dose is in the range from 0.1 mg to 2000 mg for treatment of candidiasis. In a further embodiment one or more antifungal agents selected from the group consisting of ketoconazole, miconazole and metronidazole and optionally, the agent is incorporated into a tampon.

The composition can also contain a spermicidal agent.

The compositions of the invention may also contain pharmaceutically acceptable excipients selected dependent on the particular administration route and dosage form. A person skilled in the art will with guidance from relevant pharmaceutical text books will be able to choose such excipients.

Specific Compositions

Specific compositions of the inventions are:
From 20 to 80% w/w of oligomeric lactic acid
From 2 to 35% w/w of lyophilisation agent/filler
From 20 to 60% w/w of mucoadhesive agent.
From 20 to 80% w/w of oligomeric lactic acid
From 2 to 20% w/w of lyophilisation agent/filler
From 20 to 60% w/w of mucoadhesive agent.
From 20 to 70% w/w of oligomeric lactic acid
From 5 to 15% w/w of lyophilisation agent/filler
From 20 to 50% w/w of mucoadhesive agent.
From 30 to 70% w/w of oligomeric lactic acid
From 5 to 15% w/w of lyophilisation agent/filler
From 30 to 50% w/w of mucoadhesive agent.
From 20 to 60% w/w of oligomeric lactic acid
From 5 to 15% w/w of lyophilisation agent/filler
From 20 to 50% w/w of mucoadhesive agent.
From 30 to 60% w/w of oligomeric lactic acid
From 5 to 15% w/w of lyophilisation agent/filler
From 30 to 50% w/w of mucoadhesive agent.
From 30 to 50% w/w of oligomeric lactic acid
From 7 to 12% w/w of lyophilisation agent/filler
From 35 to 50% w/w of mucoadhesive agent.
From 30 to 40% w/w of oligomeric lactic acid
From 7 to 12% w/w of lyophilisation agent/filler
From 35 to 45% w/w of mucoadhesive agent.
About 35-36% w/w of oligomeric lactic acid
About 9-10% w/w of lyophilisation agent/filler
About 35-45% w/w of mucoadhesive agent.

The oligomeric lactic acid is as described herein.

The lyophilisation agent/filler may be lactose. The mucoadhesive agent may be HPMC, notably HPMC 15 cP. The compositions mentioned above may contain one or more pH-adjusting or buffering agents. If present, the concentration of such an agent is normally from about 2 to about 20% w/w, from about 5 to about 20% w/w or from about 10 to about 15% w/w.

Moreover, the compositions mentioned above may contain a buffer such as sodium lactate in a concentration of from 5 to 20% w/w, notably from 10-20% w/w such as 14-15% w/w.

More specific examples are seen in the examples herein.

Oligomers of Lactic Acid

The present invention also relates to specific oligomers of lactic acid, which to the best of the inventors' knowledge are novel compounds.

More specifically, the invention also provides:

An oligomeric lactic acid with the following formula

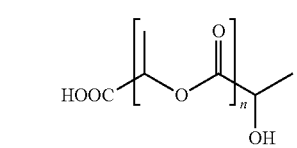

wherein n is an integer from 2 to 20, from 2 to 19, or from 2 to 18, and wherein from about 10 to about 20% w/w of the total weight of the oligomeric lactic acid is a trimer, $HL_3$, having n equal to 2. Moreover, the number average molecular weight should be in a range of from about 200 to about 500, the degree of polymerization PDn should be at the most 4.1 and the molecular weight distribution should not be too narrow, i.e. a specific oligomeric acid contains a range of oligomers with n in a range of from 1 to 13. The polydispersity index should be 1.45 or more.

In particular, the number average molecular weight should be in a range of from about 200 to about 240, the weight average molecular weight should be in a range of from about 290 to about 500, the polydispersity index should be in a range of from 1.45 to 2.5, and the degree of polymerisation should be from 2.5 to 3.8.

The number average molecular weight may also be in a range of from about 255 to about 425, the weight average molecular weight is then in a range of from about 370 to 580, the polydispersity index in a range of from 1.45 to 2.5, and the degree of polymerization should be from 3 to 4.1.

In the following are given specific oligomeric lactic acids with a constitution that enables that any of the above mentioned specifications can be met.

An oligomeric lactic acid of the present invention comprises:
from 10 to 20% w/w of $HL_2$ (i.e. n=1)
from 10 to 20% w/w of $HL_4$ (i.e. n=3)
from 10 to 15% w/w of $HL_5$ (i.e. n=4)
from 5 to 15% w/w of $HL_6$ (i.e. n=5).

An oligomeric lactic acid of the invention may also comprise from 1% to 5% w/w of each of $HL_{10}$, and $HL_{11}$; $HL_{10}$, $HL_{11}$, and $HL_{12}$; $HL_{10}$, $HL_{11}$, $HL_{12}$, and $HL_{13}$; $H_{10}$, $HL_{11}$, $HL_{12}$, $HL_{13}$, and $HL_{14}$.

The following more specific oligomeric lactic acids have a number average molecular weight in the range of from about 255 to about 425, as mentioned above and fulfil the conditions mentioned in connection thereto:

An oligomeric lactic acid, which is OMLA 3, having the following constitution:
from 7 to 10% of $HL_1$,
from 12 to 15% w/w of $HL_2$ (i.e. n=1)
from 14 to 16% w/w of $HL_3$ (i.e. n=2)
from 11 to 16% w/w of $HL_4$ (i.e. n=3)
from 10 to 15% w/w of $HL_5$ (i.e. n=4)
from 7 to 10% w/w of $HL_6$ (i.e. n=5), and
decreasing weight percentages of $HL_7$-$HL_{18}$.

An oligomeric lactic acid of the present invention having the following formula

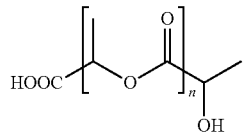

wherein
from 7 to 10% of $HL_1$ such as about 7.5
from 12 to 15% w/w of $HL_2$ (i.e. n=1) such as about 14
from 14 to 16% w/w of $HL_3$ (i.e. n=2) such as about 15.5
from 11 to 16% w/w of $HL_4$ (i.e. n=3) such as about 14
from 10 to 15% w/w of $HL_5$ (i.e. n=4) such as about 13
from 7 to 10% w/w of $HL_6$ (i.e. n=5) such as about 9, and
decreasing weight percentages of $HL_7$-$HL_{18}$.

An oligomeric lactic acid of the present invention, which is OMLA 6, having the following constitution:
from 3 to 10% of $HL_1$,
from 7 to 15% w/w of $HL_2$ (i.e. n=1)
from 10 to 15% w/w of $HL_3$ (i.e. n=2)
from 10 to 15% w/w of $HL_4$ (i.e. n=3)
from 9 to 15% w/w of $HL_5$ (i.e. n=4)
from 7 to 12% w/w of $HL_6$ (i.e. n=5), and
decreasing weight percentages of $HL_7$-$HL_{18}$.

An oligomeric lactic acid of the present invention having the following formula

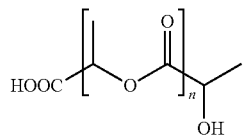

wherein
from 3 to 10% of $HL_1$ such as 5.5,
from 7 to 15% w/w of $HL_2$ (i.e. n=1) such as 9.5
from 10 to 15% w/w of $HL_3$ (i.e. n=2) such as 12
from 10 to 15% w/w of $HL_4$ (i.e. n=3) such as 12
from 9 to 15% w/w of $HL_5$ (i.e. n=4) such as 11
from 7 to 12% w/w of $HL_6$ (i.e. n=5) such as 9, and
decreasing weight percentages of $HL_7$-$HL_{18}$.

Another oligomeric lactic acid according to the invention is OMLA 22 having the following constitution:
from 5 to 10% of $HL_1$ such as from 7 to 9%
from 12 to 15% w/w of $HL_2$ (i.e. n=1) such as from 13 to 14%
from 10 to 20% w/w of $HL_3$ (i.e. n=2) such as from 15 to 16%
from 10 to 17% w/w of $HL_4$ (i.e. n=3) such as about 14%
from 9 to 15% w/w of $HL_5$ (i.e. n=4) such as about 12%
from 7 to 12% w/w of $HL_6$ (i.e. n=5) such as about 9%, and
decreasing weight percentages of $HL_7$-$HL_{18}$.

An oligomeric lactic acid of the present invention having the following formula

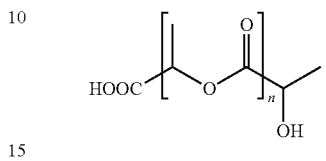

wherein
from about 5 to about 8% w/w has n=0,
from about 9 to about 14% w/w has n=1,
from about 12 to about 16% w/w has n=2,
from about 12 to about 14% w/w has n=3,
from about 11 to about 13% w/w has n=4,
from about 8 to about 10% w/w has n=5,
from about 6.5 to about 8.5% w/w has n=6,
from about 5 to about 7% w/w has n=7,
from about 4 to about 6% w/w has n=8,
and up to 100% w/w of one or more oligomers having n=9, n=10, n=11, n=12, n=13, n=14, n=15, n=16, and/or n=17.

The number average molecular weight $M_n$ of the oligomeric lactic acid, the weight average molecular weight $M_w$, the polydispersity index and the degree of polymerization are as described herein before.

Oligomeric lactic acids of the present invention are also described in detail in FIG. 3 (OMLA 3 and 6) and FIG. 5 (OMLA 22) herein, where the number average molecular weight and the polydispersity is given (OMLA 3: Mn is 258 and PDn is 3.33; OMLA 6: Mn is 313 and PDn is 4.1; OMLA 22: Mn 255 and PDn 3.29 or Mn 265 and PDn 3.43).

The oligomeric lactic acids of the present invention include all combinations of optical isomers of the oligomers of lactic acid compounds according to the present invention (e.g., R and S enantiomers, D- and L-forms), as well as racemic, diastereomeric, meso and other mixtures of such isomers.

In addition, the oligomers of lactic acid may be transformed to its corresponding esters, amides, thioesters, or salts. The salt of oligomers of lactic acid may be any pharmaceutically acceptable salt such as sodium, potassium, calcium, magnesium or ammonium, or trometamole salt. In addition, the oligomers of lactic acid may be found as complexes with metals or with macromolecules.

The oligomeric lactic acid has a water solubility of at least 1 weight percent, such as 0.1 to 50, 1 to 50 weight percent, 1 to 30 weight percent, or 5 to 30 weight percent at room temperature. The water solubility of the oligomers of lactic acid is dependent on the length of the oligomer. Moreover, the solubility may be in increased in diluted alkaline solutions Method for Preparing a Composition of the Invention The present invention also provides a method for preparing a composition as defined herein, the method comprising
i) heating water optionally together with one or more pharmaceutically acceptable excipients to about 80° C.,
ii) adding a mucoadhesive agent in small portions and mix slowly between each addition,
iii) cooling the mixture,
iv) adding oligomeric lactic acid with intermittent homogenization,
v) filling the material from iv) into forms, vi) freezing the filled form, and
vii) lyophilizing the frozen material obtained from vi).

In the manufacturing process lyophilization has been proven to be a suitable process step. However, a mixture of all components in water may also be subject to freeze-drying and the resulting material can be compressed into tablets.

The manufacturing process is described in detail in the examples herein. Other manufacturing processes may be used.

DEFINITIONS

The terms "oligomeric lactic acid" and "OMLA" are used as synonyms and are intended to mean oligomers of lactic acid with formula I and as defined herein.

However, in relation to use of oligomers of lactic acid it is envisaged that small structural variations of the oligomers do not affect their ability to release lactic acid. Accordingly, derivatives of the oligomers, wherein the terminal carboxylic acid and/or hydroxyl group has been derivatized e.g. to an ester, an amide, a thio ester (for the carboxylic acid) or an ether (for the hydroxyl group) are envisaged to be suitable for use in accordance with the invention. Accordingly, derivatives of oligomers of lactic acid with the following formula II

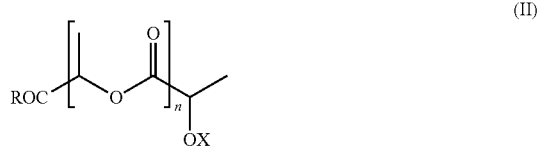

wherein n is as defined herein before for formula (I) and R is H, $R^1R^2N—$, $R^1O—$, or $R^1S—$, and $R^1$, $R^2$ and $R^3$ are the same or different and selected from H, $C_1$-$C_6$ alkyl including methyl, ethyl, propyl, isopropyl, butyl, isobutyl, tert. butyl, pentyl, hexyl, or aryl including benzyl, and pharmaceutically acceptable salts thereof, and X is H or alkyl including methyl, ethyl, propyl, isopropyl, butyl, isobutyl, tert. butyl, pentyl, hexyl, or acyl, $—OCR^4$, wherein $R^4$ is selected from H, $C_1$-$C_6$ alkyl including methyl, ethyl, propyl, isopropyl, butyl, isobutyl, tert. butyl, pentyl, hexyl, or aryl including benzyl, and pharmaceutically acceptable salts thereof, provided that R is not OH when X is H, may also be used in combination or as substitution for the lactic acid oligomers of formula (I) described herein.

By the term "antimicrobial" is intended to mean an effect that destroys or inhibits the growth of microbes, such as bacteria (e.g. Group B *Streptococcus*), fungi, viruses, or parasites. By the term "antibacterial" is intended to mean an effect that destroys or inhibits the growth of bacteria. By the term "antifungal" is intended to mean an effect that destroys or inhibits the growth of fungi. By the term "antiviral" is intended to mean an effect that destroys or inhibits the ability of a virus to replicate and, hence, inhibits its capability to multiply, reproduce or grow.

By the term "weight average molecular weight" or "$M_w$" is intended to be a description of the molecular weight of a polymer. The weight average molecular weight is calculated as: $M_w=\Sigma_i(N_iM_i^2)/\Sigma_i(N_iM_i)$ wherein $N_i$ is the number of molecules of molecular weight $M_i$. Intuitively, if the weight average molecular weight is w, and you pick a random monomer, then the polymer it belongs to will have a weight of w on average. The weight average molecular weight can be determined by e.g. mass spectrometry, NMR spectroscopy, light scattering, small angle neutron scattering (SANS), X-ray scattering, and sedimentation velocity.

By the term "number average molecular weight" or "$M_n$" is intended mean a determination of the molecular weight of a polymer. The number average molecular weight is the common, mean, average of the molecular weights of the individual polymers. It is determined by measuring the molecular weight of n polymer molecules, summing the weights, and dividing by n: $M_n=\Sigma_i(N_iM_i)/\Sigma_i(N_i)$ wherein $N_i$ is the number of molecules of molecular weight $M_i$. The number average molecular weight of a polymer can be determined by e.g. mass spectrometry, NMR spectroscopy, vapor pressure osmometry, end-group titration, and colligative properties.

By the term "polydispersity index" is intended to mean a measure of the distribution of molecular weights in a polymer sample, which is determined as the ratio of the weight average molecular weight to the number average molecular weight of a polymer.

The term "degree of polymerization", $PD_n$, is the number average molecular weight divided by the molecular weight of the monomer unit. $PD_n=(M_n-18)/72$ The terms "formulation" and "composition" is used interchangeably and mean a composition comprising one or more oligomeric lactic acid together with a mucoadhesive agent and, optionally, one or more pharmaceutically acceptable excipients or such which can be accepted for topical use to the skin or mucosa. A composition according to the invention may be presented in any suitable form, notably for administration to the vagina including vaginal administration.

By the term "antiadhesion agent" is intended to mean any agent that will reduce the adhesion properties of gynaecological pathogenic microbial organisms or virus and in particular agents that will cause such organism or virus to disadhere.

By the term "adhesiveness" is intended to mean the effect that provides or promotes adhesion or "stickiness" to a surface, such as the mucosa. For the adhesion to the mucosa the term "mucoadhesiveness" can be also used.

By the term "composition for vaginal administration" is intended to mean a drug, which is introduced to the vagina where the active ingredients are released and absorbed and will act on the mucosa; many different forms can be used including vagitorium and "pessary", which is used as a synonym.

Method of Treatment

The compositions and novel oligomeric lactic acids may be used in the treatment of the diseases and conditions mentioned herein.

Thus, they may be used in a method for the prophylaxis and/or treatment of a gynaecological infection, the method comprising administering to a subject in need thereof an effective dose of an oligomeric lactic acid as defined herein, optionally in form of a composition as defined herein.

The invention also provides a method for the management, prophylaxis and/or treatment of odour from vaginal discharge, the method comprising administering to a subject in need thereof an effective dose of an oligomeric lactic acid as defined herein, optionally in form of a composition as defined herein.

The present invention also provides a method for the management, prophylaxis and/or treatment of odour from vaginal discharge, the method comprising administering to a subject in need thereof an effective dose of an oligomeric lactic acid ad defined herein, optionally in form of a composition as defined herein, and wherein the composition comprises a sanitary device.

LEGEND OF FIGURES

FIG. 1—Flow Chart of Manufacturing Process and Process Controls

FIG. 2—dosage regimen from Example 5

FIG. 3—Oligomer distribution together with average molecular weight $M_n$ and polymerization degree $PD_n$ for the batches used in the formulations (OMLA 3 and 6)

Figure 4:
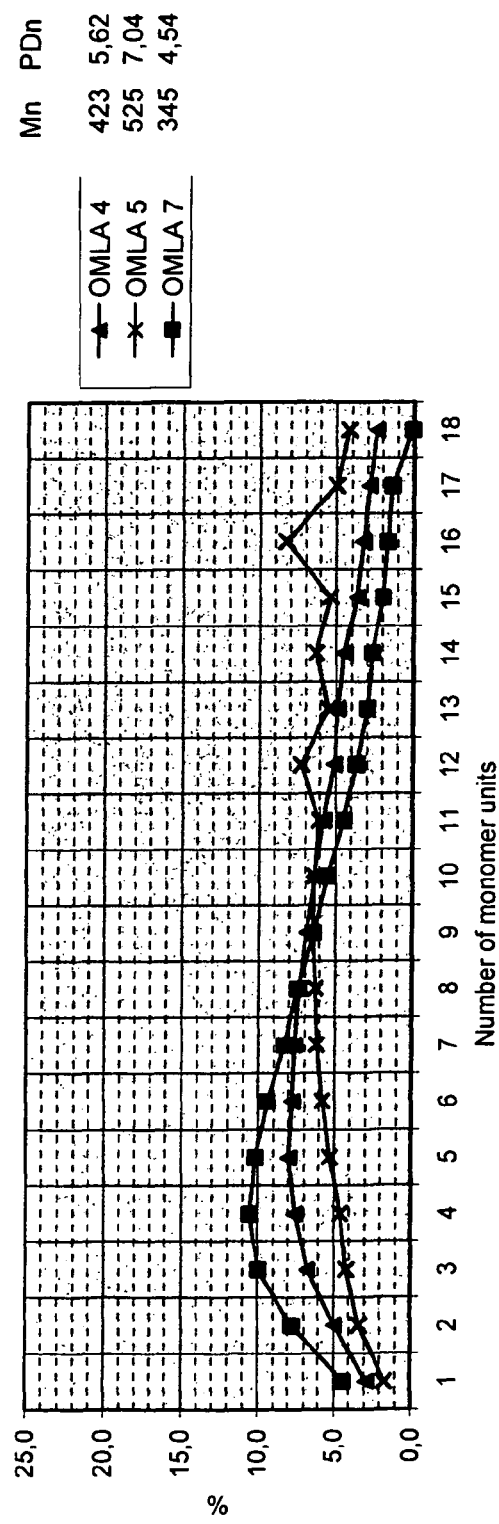

FIG. 4—Oligomer distribution together with average molecular weight $M_n$ and polymerization degree $PD_n$ for the batches that could not be used in the formulations (OMLA 4, 5, and 7)

FIG. 5—Oligomer distribution together with average molecular weight $M_n$ and polymerization degree $PD_n$ for batches (OMLA 21, and 22).

Figure 6:
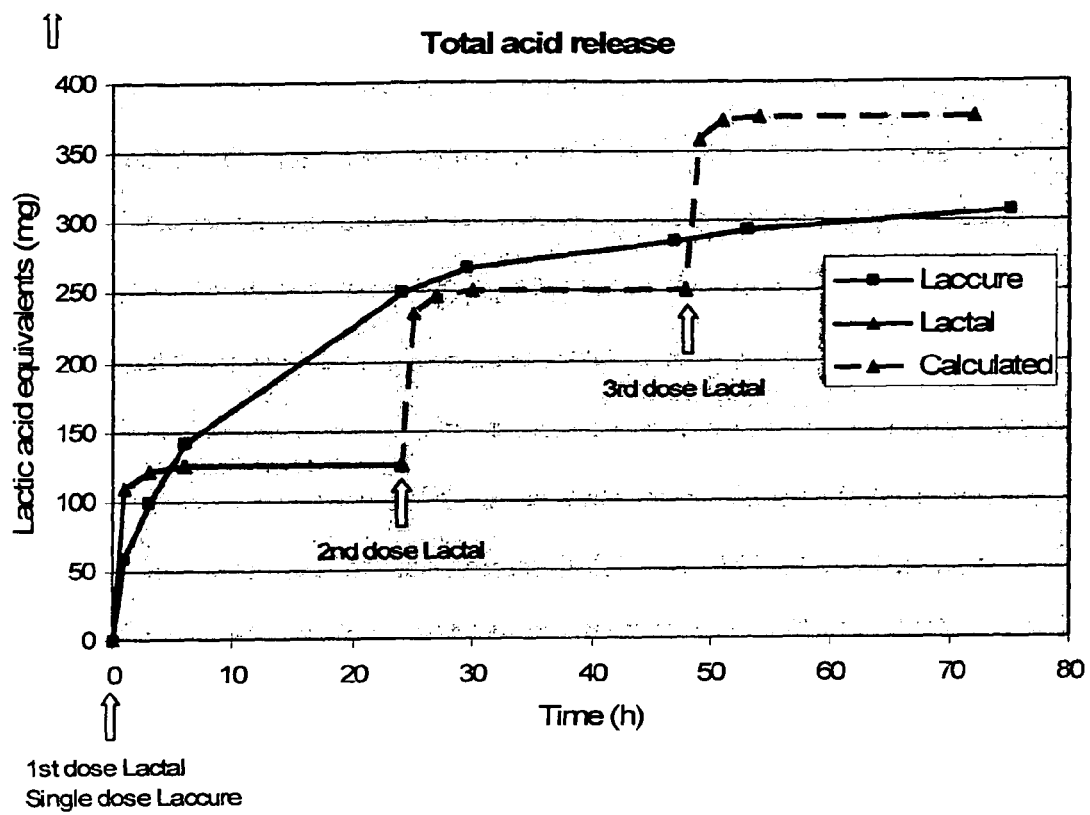

FIG. 6—Release of total acid, calculated as amount of lactic acid (mg), from Laccure vaginal tablet and Lactal vaginal gel in 900 ml water at pH 3.5 to 5.5

Figure 7:
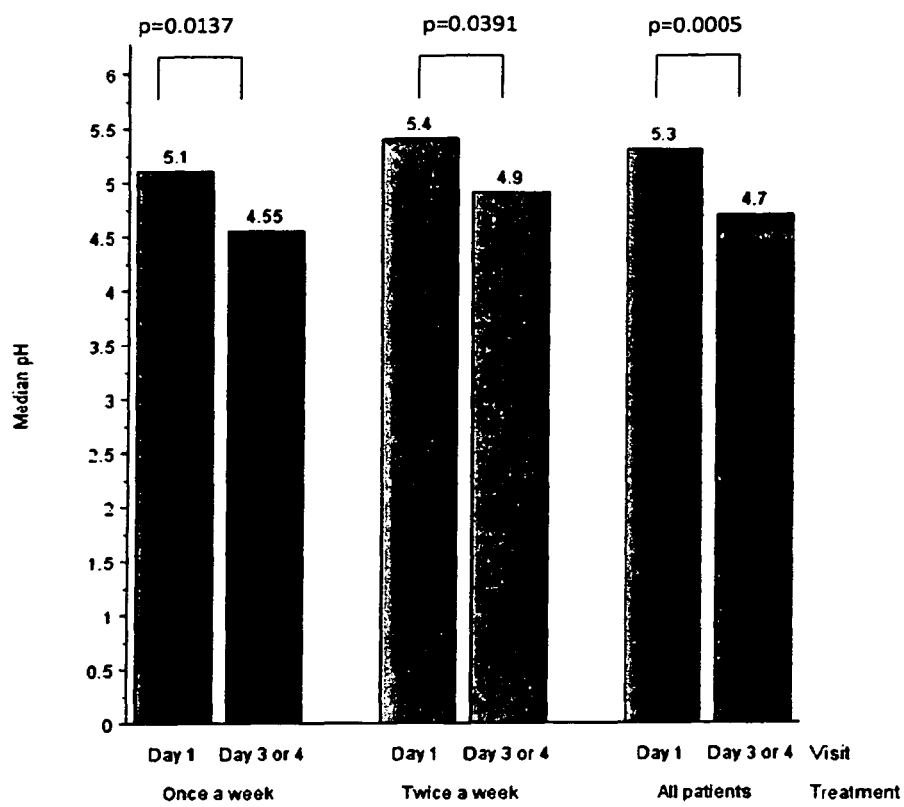

FIG. 7—Median pH value (MV) including p-values

Figure 8:
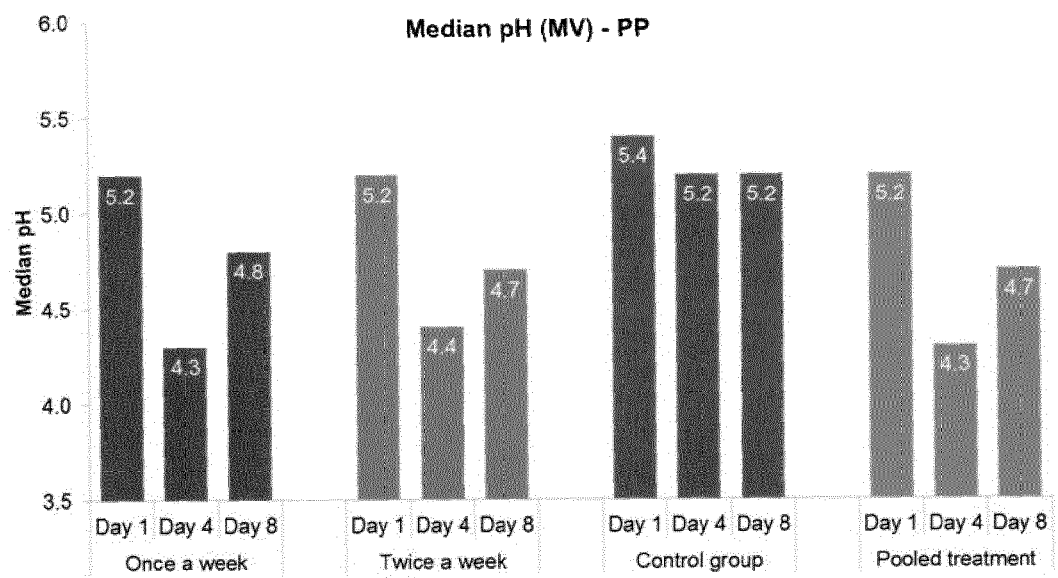

FIG. 8—Highly statistically significant decrease in pH values

Figure 9:
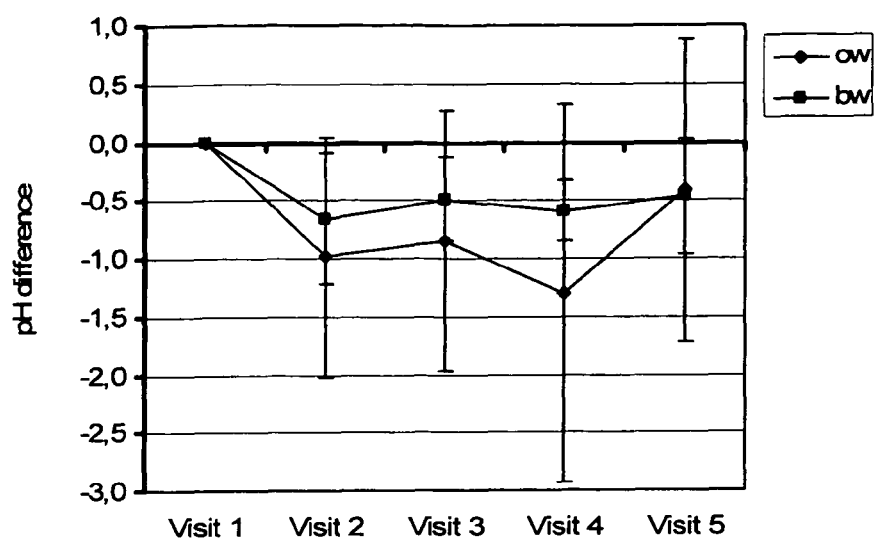

FIG. 9—Vaginal pH decrease from Visit 1 (mean value and 95% confidence interval) during treatment once a week (ow) and twice a week (bw) with Laccure vaginal tablet The invention will now be further described and illustrated by reference to the following examples, which have been carefully selected in order to encompass the invention. Accordingly, they should not be construed as limiting the invention in any way.

Methods and Analytical Procedures

Appearance

The appearance of the Oligomeric lactic acid Vaginal tablets are evaluated by visual inspection.

Identification

The identity of Oligomeric lactic acid Vaginal tablets is verified by the positive reaction for lactates according to Ph. Eur. 2.3.1.

Assay for Oligomeric Lactic Acid

The determination of free acids is performed by non-aqueous titration with potassium methylate in methanol at a pH of 8.4.

The determination of total acids is performed by titration. An excess of NaOH is added to hydrolyse the oligomers and the solution is titrated with HCl.

The difference between the free acid and the total acid gives information about the total amount of lactic acid which is bound and therefore not available as acid. The assay for oligomeric lactic acid is calculated on the anhydrous basis using the difference between the free acid and the total acid and the molecular weight for the lactate monomer and the amount of free acids and the molecular weight for the lactic acid.

Degree of Polymerisation

The degree of polymerisation is determined by dividing the total acid content by the free acid content. (Both determined by titration according to description above.)

Uniformity of Mass

The uniformity of mass is determined according to Ph. Eur. 2.9.5.

Water Content

The water content in a formulation is determined by means of volumetric Karl Fischer titration according to Ph. Eur. 2.5.12 Method A using chloroform as solvent.

pH

The formulation is dissolved in 25 ml water. The pH is determined according to Ph. Eur. 2.2.3.

Dissolution

The dissolution is performed in 900 ml 0.9% NaCl at 37° C. using paddles set at 100 rpm (Ph. Eur. 2.9.3 Apparatus 2). The formulation (a tablet) is equipped with a sinker in a gauze and put into the dissolution vessel together with the pH indicators bromocresol green, methyl red and bromothymol blue. At fixed time intervals, 0.5 M NaOH is added to raise the pH to 5.0-5.5. The dissolution is followed for 48 h and is evaluated as total amount of base added divided by the theoretical amount needed to hydrolyse one tablet.

Microbiological Quality

The tests for Total Aerobic Microbial Count (TAMC) and Total Combined Yeasts/Moulds Count (TYMC) are performed according to Ph. Eur. 2.6.12 curr. ed. and the tests for *Pseudomonas Aeruginose, Staphylucoccus Auveus* and *Candida albicans* according to Ph. Eur. 2.6.13 curr. ed.

Free Acid Determination of Oligomeric Lactic Acid

The method describes the determination of free acid in L-lactic acid oligomer by means of non-aqueous titration with potassium methylate.

Equipment

Titrator Metrohm 716 DMS Titrino

Electrode Solvotrode Metrohm 6.0229.100. Combined LL pH glass electrode, reference electrolyte LiCl in ethanol Balance Suitable balance with an accuracy better than 0.001 g Equivalent equipment may be used.

Evaluations

Calculation of free acid

Calculate the amount of free acid according to equation below:

$$FA = \frac{V \times C}{m} \text{ (mol/g)}$$

where

FA=Assay for free acids (mol/g)

V=Volume of potassium methylate needed to obtain pH 8.4 (mL)

C=Concentration of potassium methylate (mol/L)

m=Weight of sample (mg)

Total Acid Determination of Oligomeric Lactic Acid

The method describes the determination of total amount of lactic acid in L-lactic acid oligomer. An excess of NaOH is added to saponify the oligomers and the solution is then titrated potentiometrically with HCl.

Equipment

Titrator Metrohm 716 DMS Titrino

Electrode Metrohm 6.0234.110 Combined LL Micro pH-glass electrode

Balance Suitable balance with an accuracy better than 0.001 g

Heating plate

Equivalent equipment may be used.

Calculations

Calculation of total acid (mol/g)

Calculate the total amount of acid in mol/g according to equation below:

$$TA = \frac{V_{NaOH} \times C_{NaOH} - V_{EPI} \times C_{HCl}}{m} \text{ (mol/g)}$$

where
$V_{NaOH}$=Total volume of NaOH added to the sample (mL)
$C_{NaOH}$=Concentration of NaOH (mol/L)
$V_{EP1}$=Total volume of HCL used in the titrations (mL)
$C_{HCl}$=Concentration of HCl (mol/L)
m=Weighed amount of sample (mg)

Calculation of assay, total lactic acid oligomers on anhydrous basis (% m/m) Calculate the assay expressed as total lactic acid oligomers on anhydrous basis according to equation below:

$$Assay = (((TA-FA) \times Mw_{Lactate}) + (FA \times Mw_{Lacticacid})) \times \left(\frac{100}{100-C_{H_2O}}\right) \text{ (\% m/m)}$$

where
$Mw_{Lactate}$=Lactate molecular weight, i.e. 72.06 (g/mol)
$Mw_{Lacticacid}$=Lactic acid molecular weight, i.e. 90.08 (g/mol)
TA=Total acid according to 7.1 (mol/g)
FA=Free acid (mol/g)
$C_{H_2O}$=Water content (% m/m)

Calculation of Average Chain Length

Calculate the average chain length (or degree of polymerisation) according to equation below:

$$PD = \frac{TA}{FA}$$

where
PD=Polymerisation degree
FA=Free acid according to method M186 (mol/g)
TA=Total acid (mol/g) determined above Calculation of L-Lactic Acid Oligomer Average Molecular Weight Calculate the L-lactic acid oligomer average molecular weight according to equation below:

$$Mw = (PD \times Mw_{Lactate}) + Mw_{H_2O}$$

where
Mw=L-lactic acid oligomer average molecular weight (g/mol)
PD=Degree of polymerisation according to above
$MW_{Lactate}$=Lactate molecular weight, i.e. 72.06 (g/mol)
$Mw_{H_2O}$=Water molecular weight, i.e. 18.02 (g/mol)

EXAMPLES

Example 1

Composition Containing Oligomeric Lactic Acid

A vaginal tablet having the following composition was prepared:

| Name of ingredient | Quantity (mg/unit) | Function | Standard |
|---|---|---|---|
| Oligomeric lactic acid | 700* | pH-regulating agent, active ingredient | In house |
| Sodium (S)-lactate | 240 | Buffering agent | Ph. Eur. |
| Lactose | 160 | Lyophilisation aid | Ph. Eur. |

| Name of ingredient | Quantity (mg/unit) | Function | Standard |
|---|---|---|---|
| Hypromellose | 680 | Thickening agent and mucoadhesive aid | Ph. Eur. |
| Target | About 1680** | | |

*Amount corresponding to lactic acid. Actual amount of oligomeric lactic acid depends on degree of polymerisation of the oligomeric lactic acid
**Target weight calculated with a degree of polymerisation of 3.5 for the oligomeric lactic acid employed Oligomeric Lactic Acid Oligomeric lactic acid is used in the medical device to decrease the pH after administration. Upon contact with water, the oligomeric lactic acid is slowly hydrolysed to the active ingredient lactic acid. The oligomeric lactic acid is essentially made as described in WO 2008/119518, but under conditions and purification procedures that favour a higher polydispersity of the end-product, The degree of polymerisation should be from about 3.0 to about 4.1 determined by titration as specified herein.

Sodium-(S)-Lactate

Sodium-(S)-lactate is used as buffering agent, preventing the formulation from being too acidic when hydrating after administration. The sodium-(S)-lactate is added to the formulation as a 50% water solution. The sodium-(S)-lactate solution is supplied by Merck Chemicals.

Lactose Monohydrate

Lactose is used as a lyophilisation aid in order to facilitate the lyophilisation as well as given rigidity and better texture to the formulation. DMV-Fonterra is the supplier of lactose monohydrate.

Hypromellose

Hypromellose is used as a thickening agent and as a mucoadhesive aid. Together with the oligomer of lactic acid, it creates a gel when the tablet hydrates after administration. The quality of the hypromellose used is Pharmacoat 615, supplied by Shin-Etsu Chemical Co., Japan. Hypromellose is hydroxypropylmethylcellulose.

Manufacturing of the Vaginal Tablet

In the following is described a suitable process for manufacturing a highly viscous liquid gel formulation, filing the gel into suitable moulds and lyophilisation of the material. A more detailed description is given in Example 2.

The formulation contains a relatively high amount of hypromellose, which together with the relatively high amount of oligomeric lactic acid makes the gel highly concentrated and viscous. In order to be able to dissolve the large amount of hypromellose, it is added to a water solution containing lactose and sodium lactate at elevated temperature where the hypromellose does not dissolve. Upon cooling, the hypromellose starts to swell and dissolve, making the solution more and more viscous. The oligomeric lactic acid is added and the cooling continued to room temperature with intermittent homogenisation in order to get a homogenous product. The cooling process is performed under vacuum conditions in order to avoid introduction of air into the gel.

The gel is filled into pre-formed plastic ovula-shaped shells and freezed using dry ice. The plastic shells are then removed before lyophilisation in order to have a large area available for sublimation during the freeze drying process.

When the primary freeze drying (lyophilisation) is finished, secondary drying is performed at room temperature during at least 24 hours in order to reduce the moisture content of the finished product before final packaging.

Packaging

A tablet is placed in an aluminium pouch, outer dimension 15×15 cm, supplied by Oliver-Tolas Healthcare Packaging, and the pouch is heat sealed.

Example 2

Manufacturing Process to Prepare a Tablet Formulation of Oligomeric Lactic Acid Batch Formula for Oligomeric Lactic Acid Vaginal Tablet

| Ingredients | Quantity (g) |
| --- | --- |
| Oligomeric lactic acid, Purasorb OL | 1400* |
| Sodium (S)-lactate 50% | 320 |
| Lactose | 1360 |
| Hypromellose, Pharmacoat 615 | 960 |
| Purified water | to 8000 |
| Target | 8000 |

*As lactic acid. Actual amount of oligomeric lactic acid is calculated based on degree of polymerisation of the raw material.

Description of Manufacturing Process

A flow chart of the manufacturing process is given in FIG. 1.

Example 3

Characterization of a Vaginal Tablet Containing Oligomeric Lactic Acid

Dissolution

The tablets prepared as described in examples 1 and 2 were subjected to dissolution test as described herein.

The release of oligomer of lactic acid and lactic acid was measured by titration as described herein. Thus, the percentage dissolved is the sum of oligomers released and lactic acid formed from the oligomers released The results are as follows:
Start of test at t=0
At t=6 hours, 20%±10% is released
At t=24 hours, 35%±10% is released, i.e. accumulated about 55% is released
At 48 hours, at least 30% is released, i.e. accumulated at least 85% is released.

Example 4

Stability of a Composition Containing Oligomeric Lactic Acid

A technical stability investigation on the formulation has been initiated—to provide supportive data on the medicinal product. The stability investigation is a 6 month study with the possibility of extending the study to 36 months.

The synopsis of the stability study can be seen in table 1 and table 2.

TABLE 1

Test storage conditions and test time points of the stability study of Oligomeric Lactic Acid Vaginal tablet in aluminium bags.

| Storage conditions | Sampling (months) | | | | | | | | |
| --- | --- | --- | --- | --- | --- | --- | --- | --- | --- |
| | 0 | 3 | 6 | 9 | 12 | 18 | 24 | 30 | 36 |
| 25° C./60% RH | x, y | x, y, w | x, y, w | x, y, w | x, y, z, w | x, y, w | x, y, z, w | (x, y, w) | (x, y, z, w) |
| 40° C./75% RH | z, w* | x, y, w | x, y, w | | | | | | |

Tests between parentheses are optional.

*The weight change of the same 3 pouches is followed during the stability study at each storage conditions.

TABLE 2

Test parameters and test methods in the stability study TS-1009-09

| Notation in Table 1 | Test Parameter | Test Method |
|---|---|---|
|  | Appearance | Visual inspection |
|  | Assay (mg oligomeric lactic acid/unit) | Titration/ |
| x | Degree of polymerisation |  |
|  | Water content | Titration |
|  | Weight change | Gravimetry weight of the same 3 bags is followed |
| y | Dissolution | throughout the stability study Titration |

Results

The stability of Oligomeric Lactic Acid Vaginal tablets that has been used in a clinical trial, is investigated in stability study. Data from the first 24 months has been evaluated and reported here. The formulation is stable and shows no degradation during the tested time period of up to 24 months at 25° C./60% RH and 6 months at 40° C./75% RH. Based on these results, a proposed shelf life for the products is suggested to be 36 months when stored at a temperature not higher than 25° C.

TABLE 3

Results for material stored at 25° C./60% RH

| Attributes | Method | Limits (shelf-life) | Units | 0 | 3 | 6 | 9 | 12 | 18 | 24 |
|---|---|---|---|---|---|---|---|---|---|---|
| Date analysed | N/A | N/A | N/A | Nov. 17, 2010 | Feb. 22, 2011 | May 18, 2011 | Aug. 29, 2011 | Nov. 22, 2011 | May 21, 2012 | Nov. 29, 2012 |
| Appearance | Visual inspection | White to off-white egg formed tablet | N/A | White eggformed tablet | White eggformed tablet | White eggformed tablet | White eggformed tablet | White eggformed tablet | White eggformed tablet | White eggformed tablet |
| Assay | M189, M190 | 630-770 | mg lactic acid/unit | 730 | 723 | 717 | 728 | 725 | 715 | 726 |
|  |  | For information | mg OMLA/unit | 627 | 619 | 615 | 624 | 622 | 611 | 618 |
| Degree of polymerisation |  | 3.0-5.0 | N/A | 3.4 | 3.6 | 3.5 | 3.5 | 3.5 | 3.7 | 3.9 |
| Average molecular weight |  | For information | g/mol | 264 | 274 | 271 | 271 | 267 | 281 | 302 |
| Water content | M188 | ≤3.0 | % | 0.3 | 0.3 | 0.6 | 0.3 | 0.3 | 0.4 | 0.4 |
| pH | M192 | 3.0-4.0 | N/A | 3.5 | 3.5 | 3.5 | 3.5 | 3.5 | 3.5 | 3.5 |
| Weight change | M116 modified | For information | % | 0 | −0.80 | +0.18 | +0.19 | +0.12 | +0.24 | +0.14 |
| Weight of 3 Al-bags with 1 unit in each |  | N/A | g | 21.4640 | 21.4212 | 21.4734 | 21.4741 | 21.4706 | 21.4767 | 21.4715 |
| Weight of 3 empty Al-bags |  | N/A | g | 16.1408 |  |  |  |  |  |  |
| Microbiological quality |  |  |  |  |  |  |  |  |  |  |
| TAMC | Ph. Eur. 2.6.12. | NMT 100 $\hat{}$ 2 | CFU/g | <100 |  |  |  | <100 |  | <100 |
| TYMC |  | NMT 10 $\hat{}$ 1 | CFU/g | <100* |  |  |  | <100* |  | <100* |
| Pseudomonas aeruginosa | Ph. Eur. 2.6.13. | Absent in 1 g | N/A | Absent |  |  |  | Absent |  | Absent |
| Staphylococcus aureus |  | Absent in 1 g | N/A | Absent |  |  |  | Absent |  | Absent |
| Candida albicans |  | Absent in 1 g | N/A | Absent |  |  |  | Absent |  | Absent |

TABLE 4

Results for material stored at 40° C./75% RH

| Attributes | Method | Limits (shelf-life) | Units | Time (months) 0 | 3 | 6 |
|---|---|---|---|---|---|---|
| Date analysed | N/A | N/A | N/A | | | |
| Appearance | Visual inspection | White to off-white egg formed tablet | N/A | Complies | Complies | Complies |
| Assay | M189, M190 | 630-770 | mg lactic acid/unit | 730 | 720 | 722 |
| | | For information | mg OMLA/unit | 627 | 617 | 620 |
| Degree of polymerisation | | 3.0-5.0 | N/A | 3.4 | 3.5 | 3.4 |
| Average molecular weight | | For information | g/mol | 264 | 269 | 262 |
| Water content | M188 | ≤3.0 | % | 0.3 | 0.2 | 0.4 |
| pH | M192 | 3.0-4.0 | N/A | 3.5 | 3.5 | 3.5 |
| Weight change | M116 modified | For information | % | 0 | −0.89 | +0.20 |
| Weight of 3 Al-bags with 1 unit in each | | N/A | g | 21.3938 | 21.3470 | 21.4045 |
| Weight of 3 empty Al-bags | | N/A | g | 16.1408 | | |

The dissolution of the material complied with the limits in both stability studies.

Appearance

The appearance of the tablet remains unchanged at both storage conditions tested.

Assay

A small decrease in assay can be seen between initial testing and testing at 3 and 6 months at both storage conditions. At 25° C./60% RH, the assay results increase again for the later analysed two time points. Therefore, it is reasonable to believe that the lower results at the intermediate time points reflect the range in precision of the analytical method. All values are well within the set specification limits.

Degree of Polymerization—Average Molecular Weight

No decrease in degree of polymerization or average molecular weight could be detected at any of the storage conditions during the period.

Water Content

All values are well below the set limits, which imply that the primary package is impermeable to moisture.

pH

No change in pH is noted during the tested period.

Example 5

A Feasibility Study in Healthy Women on OMLA Vaginal Tablet 400 mg and OMLA Pessary 500 mg Compared to Lactal and Vivag The purpose with the study was to compare two different compositions containing oligomers of lactic acid with two commercially available lactate products.

Test Products

The Vaginal tablet 400 mg was prepared using lyophilisation technique as described herein.

The composition was:

| Substance | Gel before lyophilisation mg/unit | % | Final product mg/unit | % |
|---|---|---|---|---|
| Oligomeric lactic acid (OMLA30) | 400 | 20 | 400 | 40 |
| Lactose | 200 | 10 | 200 | 20 |
| HPMC | 400 | 20 | 400 | 40 |
| Water | 1000 | 50 | — | — |
| | total mass = 2 g | | total mass = 1 g | |

Pessary 500 mg

The pessary used in the study was prepared at the Department of Pharmaceutical Technology, Academia Medical Gdansk. OMLA 30 was mixed with Macrogol 6000 and moulded in a 3 g suppository form. The composition was:

Moulded Pessary [mg]

| | |
|---|---|
| Oligomeric lactic acid (OMLA 30) | 500 |
| Macrogol 6000 | 2000 |

OMLA 30 was obtained by heating racemic lactic acid (85%) at 120° C. for 30 h (Lund University).

Reference Products

Lactal vaginal gel 5 mL (Kullgren Pharma AB, Sweden) is a Medical Device used to restore the physiological pH balance in the vagina. It contains lactic acid, glycogen, propylene glycol, methyl hydroxypropyl cellulose, sodium lactate, and water.

Vivag VG (vaginal capsules, Ferrosan AB) is a Natural Pharmaceutical traditionally used when the vaginal bacterial flora is in unbalance. It contains freeze-dried *Lactobacillus Acidophilus* together with lactose and magnesium stearate.

Both Lactal and Vivag used in the study were commercial preparations.

Study Design

The study design is shown in FIG. 2.

One subject tested OMLA pessary 500 mg, OMLA vaginal tablet 400 mg, Lactal and Vivag in that order. The subject measured pH and observed tolerability/acceptability for 4 days after the administration of the pessary and the vaginal tablet, and for 1 day after administration of Lactal and Vivag. After the administration, the time for measurement was 0, 4 h, 8 h and 12 h on each day during the observation period. There was at least one week between each test.

Measurements

The pH in the vaginal mucous was assessed by the subject using pH strips (pH-Fix 3.6-6.1, Macherey-Nagel). The subject reported the general tolerability/acceptability and the type of discomfort that was experienced.

Results

Both the vaginal tablet and the pessary lowered the vaginal pH for about 3 days. The pH lowering effect was more pronounced for the vaginal tablet. The vaginal tablet did not show any subjective discomfort, and the general tolerability/acceptability was rated "Very good". The pessary was discharged during the first 2 days after administration, and the general tolerability/acceptability was rated "Mild discomfort" and "Good but not optimal".

Lactal lowered the vaginal pH for 8 hours. Mild burning and discharge was reported during the first day after administration. The general tolerability/acceptability was rated "Good".

Vivag did not have any effect on the vaginal pH and showed no discomfort

Example 6

A Feasibility Study on OMLA Vaginal Tablets 600 mg with 2 Different Oligomer Distributions An oligomer of lactic acid has the potential of lowering vaginal pH by forming lactic acid through hydrolysis, and by direct action of the carboxylate end-group of the oligomer. This would be beneficial in situations of unphysiological high vaginal pH. A formulation of lactic acid oligomers and a suitable mucoadhesive polymer could have the possibility to lower the vaginal pH for several days.

In a previous feasibility study by one healthy woman, a vaginal tablet containing 400 mg of lactic acid oligomers showed promising pH-lowering properties. To investigate if the duration of the effect can be increased, 2 new formulations containing 600 mg of lactic acid oligomers of different distribution were manufactured and tested by 4 healthy women in the present feasibility study.

Active Ingredient

The active ingredient (OMLA) was manufactured at Lund University, Sweden.

The oligomerisation of lactic acid was achieved by heating L(+)-lactic acid (LA), supplied by Purac (PURAC PF90, product code 20706, batch no. 0609002001). This quality contains 90% LA and 10% water.

OMLA 6 and OMLA 3 were prepared by the following procedure: 50 ml LA was added to a 50 ml round bottomed flask and heated in an oil bath for various periods and at different temperatures. The flask was lowered into a hot oil bath. The time to heat the solution was approximately 10 minutes. The flask was kept open to the atmosphere during the procedure, which took place in a hood, allowing water vapour formed to escape. After that the reaction was finished the flask was taken out of the oil bath, closed with a stopper and allowed to cool to room temperature. The time to cool was approximately 20 minutes. OMLA 3 was kept at 120° C. for 18 hours and OMLA 6 at 120° C. for 24 hours.

The analyses of the oligomer distribution were performed by Purac, the Netherlands. Lactic acid, lactide, and lactic acid oligomers were separated using liquid chromatography and quantified with UV detection. The actual separation of the oligomers was performed with a gradient system in which the concentration of the organic solvent was increased during the run. The UV response of the oligomers was measured at a wavelength at which carbonyl- and ester-bonds are known to adsorb. The quantification was done using an external standard method. The results for the batches that could be used in the formulations are shown in FIG. 3 and the results for the batches that could not be used in FIG. 4. The number average molecular weight $M_n$ is the arithmetic mean of the molecular weights of the individual macromolecules. The degree of polymerisation $DP_n$ is the average number of repeat units in a polymer chain.

The test products used in the study were prepared as follows:

Lactose and HPMC (Metolose 60SH 4000 cP) was dissolved in water forming a viscous solution. OMLA 6 or OMLA 3 was added, and all was mixed using a small-size high-shear mixer during approximately half a minute. The resulting gel was applied in a mould (15 mm diameter and >15 mm high) using a syringe. The mould was placed in the lyophiliser (Christ Alpha 2-4) in −40° C. at normal pressure for 2 hours for freezing. Then the lyophiliser was evacuated to a pressure of 1 mbar and the temperature gradually increased manually (−25, −10, 0, 10° C.) until 20° C. was reached after about 42 hours, and then the pressure was further decreased to 0.1 mbar. The temperature was increased to 30° C. for 2 hours, and the process was finished.

The compositions were:

| Batch | Substance | Gel before lyophilization mg/unit | % | Final product mg/unit | % | No of units * |
|---|---|---|---|---|---|---|
| H6/1b | OMLA 6 | 600 | 20 | 600 | 57 | 4 |
|  | Lactose | 300 | 10 | 300 | 29 |  |
|  | HPMC** | 150 | 5 | 150 | 14 |  |
|  | Water | 1950 | 65 | — |  |  |
|  |  | total mass = 3 g |  | total mass = 1.05 g |  |  |
| H3/1a and H3/1b | OMLA 3 | 600 | 20 | 600 | 57 | 2 + 3 = 5 |
|  | Lactose | 300 | 10 | 300 | 29 |  |
|  | HPMC** | 150 | 5 | 150 | 14 |  |
|  | Water | 1950 | 65 | — |  |  |
|  |  | total mass = 3 g |  | total mass = 1.05 g |  |  |

**Matolose 60SH 4000 cP—high viscosity (Shin-Etsu Chemicals).

The tablets were white, cylindrical and spongy

Subjects

Four healthy women aged 51-62 years (mean 56.5 years) participated in the study.

Study Design

| OMLA 3 vaginal tablet | OMLA 6 vaginal tablet |
|---|---|
| 7 days | 7 days |

Four subjects tested first OMLA 3 and then OMLA 6 vaginal tablet 600 mg. The subjects measured pH and observed tolerability/acceptability for 7 days. After the administration, the time for measurement was 0, 4 h, 8 h and 12 h on each day during the observation period. There was at least one week between the administrations.

pH Measurements

The pH in the vaginal mucous was self-assessed by the subjects using pH strips (pH-Fix 3.6-6.1 manufactured by Macherey-Nagel).

Tolerability/Acceptability

The subjects reported the general tolerability/acceptability together with a comment on the type of discomfort that was experienced.

Results pH Measurements

OMLA 3

All four subjects had a decreased vaginal pH during the first day.

Two subjects showed duration of the pH-lowering effect of about 6 and 3 days, respectively.

OMLA 6

All four subjects had a decreased vaginal pH during the first day.

Two subjects showed duration of the pH-lowering effect of 7 days or more.

Two subjects reported that the tablet feel out during swimming and jogging.

Example 7

A Feasibility Study on OMLA Vaginal Tablets 600 mg with High Content of Cellulose Polymer: I In a previous feasibility study by one healthy woman a vaginal tablet containing 400 mg of lactic acid oligomers showed promising pH-lowering properties. In a subsequent feasibility study (reported in Example 7), two new formulations containing 600 mg of lactic acid oligomers of different distribution were tested by 4 healthy women. The formulations showed prolonged duration compared to the first study but were experienced as less mucoadhesive and had a tendency to fall out.

Therefore a new formulation with a higher content of cellulose polymer to increase the mucoadhesiveness was manufactured and tested in the present feasibility study. This report concerns the first part of the study in which the cellulose polymer was Metolose 60SH 15 cP.

Active Ingredient

Three batches of the active ingredient (OMLA) were manufactured by Purac biomaterials, Gorinchem, the Netherlands. They were stored at −15° C. for 7 months These batches were labelled OMLA 21 and OMLA 22. OMLA 22 was used in the present study since it was most close to the OMLA used in the previous study with regard to the polymerisation degree. FIG. 5 show the molecular weight distribution of these oligomeric lactic acids as well as relevant data.

The analyses of the oligomer distribution were performed by Purac. Lactic acid and lactic acid oligomers were separated using liquid chromatography and quantified with UV detection. The actual separation of the oligomers was performed with a gradient system in which the concentration of the organic solvent was increased during the run. The UV response of the oligomers was measured at a wavelength at which carbonyl- and ester-bonds are known to adsorb. The quantification was done using an external standard method.

The results of the analyses are shown in FIG. 5. The initial analyses and the analyses after 7 months at −15° C. are in very good agreement.

The number average molecular weight $M_n$ is the arithmetic mean of the molecular weights of the individual macromolecules. The degree of polymerisation $DP_n$ is the average number of repeat units in a polymer chain.

Formulations

The test product used in the present study was prepared using the following procedure:

Lactose and HPMC (Metolose 60SH 15 cP) was dissolved in water forming a viscous solution. OMLA 22 was added, and all was mixed using a small-size high-shear mixer during approximately half a minute. The resulting gel was applied in a mould (a tube of 16 mm diameter with rounded tip and <20 mm high) using a syringe. The mould was placed in the lyophiliser (Christ Alpha 2-4) in −40° C. at normal pressure for 2 hours for freezing. After that the lyophiliser was evacuated to a pressure of 1 mbar and the temperature gradually increased manually (−25, −10, 0, 10° C.) until 20° C. was reached after about 42 hours, and then the pressure was further decreased to 0.1 mbar. The temperature was increased to 30° C. for 2 hours, and the process was finished.

The composition of the test product was:

| Substance | Gel before lyophilisation | | Final product | | Nr of units* |
| --- | --- | --- | --- | --- | --- |
| | mg/unit | % | mg/unit | % | |
| OMLA 22 | 600 | 15 | 600 | 41 | 6 |
| Lactose | 170 | 4 | 170 | 12 | |
| HPMC 15 cP** | 680 | 17 | 680 | 47 | |
| Water | 2550 | 64 | — | — | |
| | total mass = 4 g | | total mass = 1.45 g | | |

**Metolose 60SH 15 cP - low viscosity (Shin-Etsu Chemicals) - corresponds to Hypromellose 615.

Subjects

Four healthy women aged 52-63 years (mean 57.5 years) participated in the study.

Study Design

Four subjects tested the OMLA vaginal tablet 600 mg. The subjects measured pH and observed tolerability/acceptability for at least 7 days. The pH was measured at four time points the day before the administration to obtain baseline pH.

pH Measurements

The pH in the vaginal mucous was self-assessed by the subjects using pH strips (pH-Fix 3.6-6.1 manufactured by Macherey-Nagel).

Tolerability/Acceptability

The subjects reported the general tolerability/acceptability together with a comment on the type of discomfort that was experienced.

Results pH Measurements

In 3 of the 4 subjects the duration of the pH-lowering effect was longer than one week. In the fourth subject there was a pH-lowering effect during the first day.

Tolerability/Acceptability

One subject experienced a little burning after 2 hours during the first day, and two subjects had discharge and felt smeary during the first 2-3 days. The tolerability/acceptability was mostly rated "Very good".

The studies show that HPMC with the grade 15 cP is very suitable for obtaining the desired result.

Example 8

A Feasibility Study on OMLA Vaginal Tablets 600 mg with High Content of Cellulose Polymer: II The study was made in accordance with the details given above in Example 7. However, another formulation was tested, namely:

| Substance | Gel before lyophilisation mg/unit | % | Final product mg/unit | % | Nr of units* |
|---|---|---|---|---|---|
| OMLA 22 | 600 | 15 | 600 | 41 | 6 |
| Lactose | 170 | 4 | 170 | 12 | |
| HPMC 6 cP** | 680 | 17 | 680 | 47 | |
| Water | 2550 | 64 | — | — | |
| | total mass = 4 g | | total mass = 1.45 g | | |

**Pharmacoat 606 - low viscosity (Shin-Etsu Chemicals).

Subjects

Four women aged 52-63 years (mean 57.5 years) participated in the study.

Results pH Measurements

In 2 of the 4 subjects the duration of the pH-lowering effect was about 4-5 days. In the two other subjects it was about 1.5 days.

Example 9

In Vitro Comparison Between Laccure Vaginal Tablet and Lactal Vaginal Gel

Lactobacilli dominate the normal vaginal ecosystem. A low vaginal pH, less than 4.5, is maintained by lactic acid produced by this flora and protects against infection by other species. A disturbance in this ecosystem may result in an overgrowth by other bacteria, e.g. *Gardnerella*, which is followed by an increasing pH above 4.5, typically between 5 and 6. This condition is called bacterial vaginosis, or BV, and it is characterised by a strong foul fishy odour often combined with excessive vaginal discharge and elevated vaginal pH.

The current therapy that women with BV receive when they visit gynaecologists is dominated by antibiotics. However, most women try to manage their problems without the help of specialists, and they often use a pH-regulating product to restore the physiological low pH below 4.5. Lactal vaginal gel is a widely used non-prescription product which is based on lactic acid in hypromellose. Lactal is administered every day for 7 days.

Laccure AB has developed a new product, Laccure vaginal tablet. In this product, lactic acid, condensed to lactic acid oligomers, is included together with sodium lactate, hypromellose and lactose, and it is freeze-dried to a solid ovulo-shaped vaginal tablet. When in contact with water in the vaginal mucus, lactic acid oligomers, sodium lactate and hypromellose are slowly released from the tablet, forming a mucoadhesive gel buffered to pH 3.5 attaching to the vaginal mucosa. Laccure vaginal tablet is designed to have a dosing interval of at least 3-4 days, optimally 7 days.

The present investigation compares a vaginal tablet according to the invention and Lactal vaginal gel with regard to content of lactic acid, pH after dissolution in water and release of total acid.

Vaginal Tablet

The batch used in this investigation was manufactured as a confirmatory batch before manufacturing of the batches for the clinical study. It was also used for stability studies. The composition is given in the following table.

TABLE 5

Composition of the Laccure vaginal tablet.

| Raw materials | Amount |
|---|---|
| Oligomeric lactic acid Purasorb OL | 600 mg* |
| Sodium lactate | 240 mg |
| Hypromellose Pharmacoat 615 | 680 mg |
| Lactose, monohydrate | 160 mg |
| TOTAL WEIGHT | 1680 mg |

*Corresponds to 700 mg lactic acid

Lactal Vaginal Gel

Lactal vaginal gel (batch no. 10-029) was purchased at a local pharmacy in Malmö, Sweden. A dose unit of Lactal is a tube with 5 mL gel containing lactic acid and hypromellose and buffered with sodium lactate to about pH 3.5.

Methods

The test methods used in this investigation are the same as the product specification methods used for the release of vaginal tablet (Table 2).

TABLE 6

Tests and methods.

| Test | Method/Procedure |
|---|---|
| Weight | — |
| Assay for oligomeric lactic acid | See method and analysis paragraph |
| Degree of polymerisation | See method and analysis paragraph |
| pH | Ph. Eur. 2.2.3., curr. ed. See method and analysis paragraph |
| Dissolution | Titration/See method and analysis paragraph |

Results

The results of the tests, except for the dissolution of total acid, are shown in the following table. The weight of one dose unit of vaginal tablet is about 3 times lower than one dose unit of Lactal vaginal gel, but the total content of lactic acid is about 6 times higher in the vaginal tablet than in Lactal. The pH after dissolving in water for 24 hours is about the same. The degree of polymerisation of lactic acid in the vaginal tablet is 3.5, while Lactal contains very little lactic acid oligomers.

TABLE 7

Test results

| Test | vaginal tablet (batch 83601-1009-14) | Lactal vaginal gel (batch 10-029) |
|---|---|---|
| Weight per unit | 1.71 g | 4.71 g |
| Amount lactic acid per unit | 739 mg | 125 mg |
| Degree of polymerisation | 3.5 | 1.2 |
| pH (20 h in 20 mL water) | 3.6 | 3.8 |

FIG. 6 shows the dissolution of total acid from vaginal tablet during 75 hours, and the calculate release from lactal vaginal gel during the same time period. The release of acidifying agent from Laccure vaginal tablet was about 150 mg lactic acid equivalents after 6 h, about 250 mg after 24 h, and about 310 mg after 72 h. This was similar to accumulated release from three doses of Lactal given once daily.

Conclusions

The total content of lactic acid is about 6 times higher in Lactal vaginal tablet than in Lactal vaginal gel, which agrees with dosing once a week for Laccure vaginal tablet. When dissolved in water, the vaginal tablet achieves about the same pH as Lactal vaginal gel.

The amount of acidifying agent released in vitro from Laccure vaginal tablet during the first 72 hours was similar to accumulated release from three doses of Lactal given once daily.

Example 10 pH Regulating Effect and Safety of Vaginal Tablet Containing Oligomers of Lactic Acid in Patients with Bacterial Vaginosis. An Open Controlled Study with Parallel Groups. Study a Study Objectives
Primary Objective To assess the safety of Laccure vaginal tablet in subjects with bacterial vaginosis (BV).

Secondary Objective

To assess the tolerability (acceptability/user friendliness) and efficacy of Laccure vaginal tablet in subjects with bacterial vaginosis (BV).

Primary Endpoint

Adverse events reported spontaneously and adverse events reported upon vulvovaginal examination at the final visit.

Secondary endpoints:

Normalisation of vaginal pH (4.5 or below) at one and two weeks

Acceptability/user friendliness of the tablet through a subject diary

The efficacy of the tablet is also established using Amsel's criteria.

This is assessed by measuring the proportion of patients at one and two weeks for each of the following criteria:

1. Thin, white, yellow, homogeneous discharge
2. Clue cells on microscopy
3. Release of a fishy odour on adding alkali—i.e. 10% potassium hydroxide (KOH) solution Moreover, the fourth of Amsel's criteria is a pH of vagina fluid >4.5, but it is not mentioned above, as pH has been addressed in the secondary endpoint above Clue cells are epithelial cells of the vagina that get their distinctive stippled appearance by being covered with bacteria. Clue cells are a medical sign of bacterial vaginosis, particularly that caused by *Gardnerella vaginalis*, a group of Gram-variable bacteria. This bacterial infection gives a foul, fishy smelling, thin vaginal discharge. Also the vaginal pH is increased often above 5.5. Normal vaginal pH varies around 4.5.

The proportion of patients, who have BV, will be confirmed if 3 out of 4 Amsel's criteria are fulfilled.

Study Design

The study design is adaptive and contains two parts, Part A and Part B. Part A There were two different groups of subjects in Part A;

Group 1 (10 patients): Subjects with ongoing BV that were treated with Laccure vaginal tablet once a week for two weeks.

Group 2 (10 patients): Subjects with ongoing BV that were treated with Laccure vaginal tablet twice a week for two weeks.

Subjects with ongoing BV were randomised to groups 1 or 2. Amsel's criteria were used to diagnose BV.

If at least three of the following criteria were fulfilled, the patient was diagnosed to have ongoing BV.

1. Thin, white, yellow, homogeneous discharge
2. Clue cells on microscopy
3. Release of a fishy odour on adding alkali—i.e. 10% potassium hydroxide (KOH) solution
4. pH above 4.5

Inclusion Criteria

Females at least 18 years of age

Confirmed current diagnosis of bacterial vaginosis (determined at study screening) using Amsel's criteria Subjects who are willing to refrain from the use of all other vaginal products throughout the study except for intrauterine device Must abstain from sexual intercourse or use condom throughout the duration of the study Women of child bearing potential must have a negative urine pregnancy test result upon entry into the study.

Subject is willing to answer questions mainly related to product acceptability but some that are related to sexual activity.

Subjects who are able to give written informed consent and agree to follow-up on time.

Results
Subjects

Two patients in the group once a week did not complete the study, one due to adverse event and one due to menstruation during the study. One patient did not complete the study in the twice a week group due to adverse event. Almost all patients did attend every visit; at day 10, 3 patient did not attend in the Once a week group and 2 patients did not attend in the Twice a week group.

TABLE 8

Number of subjects who fulfilled the study

|  | Once a week | | Twice a week | | All | |
| --- | --- | --- | --- | --- | --- | --- |
|  | n | % | n | % | n | % |
| Did the patient complete the study | | | | | | |
| No | 2 | 18.2 | 1 | 10.0 | 3 | 14.3 |
| Yes | 9 | 81.8 | 9 | 90.0 | 18 | 85.7 |
| Total | 11 | 100.0 | 10 | 100.0 | 21 | 100.0 |

Baseline Characteristics and Demographics

Mean age in once a week group was 33 years and 29 years for the twice a week group. All patients except for two (Black, Latino) were Caucasian. All patients had a confirmed BV according to Amsel's criteria at visit 1.

At day 1 the following results were obtained:

TABLE 9

Individual Amsel's criteria—Thin, white, yellow, homogenous discharge at Day 1

|  | Once a week | | Twice a week | | All | |
| --- | --- | --- | --- | --- | --- | --- |
|  | n | % | n | % | n | % |
| No | 0 | 0 | 1 | 10.0 | 1 | 4.8 |
| Yes | 11 | 100.0 | 9 | 90.0 | 20 | 95.2 |

TABLE 10

Individual Amsel's criteria—Clue cells on microscopy at Day 1

|  | Once a week | | Twice a week | | All | |
| --- | --- | --- | --- | --- | --- | --- |
|  | n | % | n | % | n | % |
| No | 0 | 0 | 2 | 20.0 | 2 | 9.5 |
| Yes | 11 | 100.0 | 8 | 80.0 | 19 | 90.5 |

TABLE 11

Individual Amsel's criteria pH of vaginal fluid >4.5 at Day 1 according to CRF

|  | Once a week | | Twice a week | | All | |
| --- | --- | --- | --- | --- | --- | --- |
|  | n | % | n | % | n | % |
| Yes | 11 | 100.0 | 10 | 100.0 | 21 | 100.0 |

TABLE 12

Individual Amsel's criteria—Release of a fishy odour on adding alkali—10% potassium hydroxide (KOH) solution at Day 1

|  | Once a week | | Twice a week | | All | |
| --- | --- | --- | --- | --- | --- | --- |
|  | n | % | n | % | n | % |
| No | 0 | 0 | 1 | 10.0 | 1 | 4.8 |
| Yes | 11 | 100.0 | 9 | 90.0 | 20 | 95.2 |

TABLE 13

Amsel's criteria fulfilled at Day 1

|  | Once a week | | Twice a week | | All | |
| --- | --- | --- | --- | --- | --- | --- |
|  | n | % | n | % | n | % |
| Yes | 11 | 100.0 | 10 | 100.0 | 21 | 100.0 |

Primary Endpoint—pH
pH Values in the Middle of the Vagina (MV)

pH was measured with a pH electrode. In many publications pH is measured with lacmus paper, which is a less sensitive method.

Only 5 patients reached a pH below 4.5 from visit 1 to visit 2 in the once a week group and 4 patients in the twice a week group. The corresponding figures for the classification of pH below 4.7 were 6 and 4 respectively. All patients had sometimes during the study a lower pH value compared to visit 1.

The mean pH level at visit 1 was 5.6 for the once a week group and 5.3 for the twice a week group. The change between visit 1 and visit 2 for the once a week group was −0.99 and −0.66 for the twice a week group. This reduction in the pH level was the highest of all comparisons, besides visit 4, but at visit 4, 3 patients had missing values in the once a week group and 2 in the twice a week group.

pH Values (MV) Comparison of Day 1 and Day 3 or 4

The graph below shows the median pH values (MV) at day 1, and day 4. Alternatively, if day 4 was not an option, pH was measured on day 3, respectively. The p-values from the Wilcoxon signed rank test are also included in the graph. The differences between day 1 and day 3 or 4 are statistically significant (p<0.05), in both treatment groups, and also when combining the two treatment groups. This indicates that there is an initial effect on the pH values (MV) when using Laccure vaginal tablet. A similar pattern was received when plotting the mean values.

The decrease in pH value is given in FIG. 7.

Secondary Efficacy Endpoint
Bacterial Vaginosis
Amsel's Criteria BV Confirmed

All patients in the once a week group had no BV at visit 3, and 8 patients had no BV at visit 5. In the twice a week group nine patients had no BV at visit 3 and at visit 5, respectively.

TABLE 14

Amsel's criteria—BV, confirmed at week 1 and week 2

| Visit | Bacterial vaginosis {BV} confirmed | Once a week | | Twice a week | | All | |
| --- | --- | --- | --- | --- | --- | --- | --- |
|  |  | n | % | n | % | n | % |
| Visit 3, Day 8 | No | 10 | 100.0 | 9 | 90.0 | 19 | 95.0 |
|  | Yes | 0 | 0 | 1 | 10.0 | 1 | 5.0 |
|  | Total | 10 | 100.0 | 10 | 100.0 | 20 | 100.0 |
| Visit 5, Day 15 | No | 8 | 80.0 | 9 | 100.0 | 17 | 89.5 |
|  | Yes | 2 | 20.0 | 0 | 0 | 2 | 10.5 |
|  | Total | 10 | 100.0 | 9 | 100.0 | 19 | 100.0 |

TABLE 15

Patients with no BV at one and two weeks, respectively - including exact 95% CI

| Visit | Treatment | number with no BV | % | Exact 95% confidence interval |
| --- | --- | --- | --- | --- |
| Visit 3, Day 8 | Once a week | 10 | 100.0 | (69.2-100.0) |
|  | Twice a week | 9 | 90.0 | (55.5-99.7) |
| Visit 5, Day 15 | Once a week | 8 | 80.0 | (44.4-97.5) |
|  | Twice a week | 9 | 100.0 | (66.4-100.0) |

Amsel's Criteria—Thin, White, Yellow, Homogeneous Discharge

All patients in the once a week group had no "thin, white, yellow, homogenous discharge" at visit 3, however the criteria was present for 3 patients at visit 5. In the twice a week group eight patients had no "thin, white, yellow, homogenous discharge" at visit 3 and visit 5, respectively.

TABLE 16

Individual Amsel's criteria—thin, white, yellow, homogeneous discharge, by visit

| Visit | Thin, white, yellow, homogenous discharge | Once a week | | Twice a week | | All | |
| --- | --- | --- | --- | --- | --- | --- | --- |
|  |  | n | % | n | % | n | % |
| Visit 1, Day 1 | No | 0 | 0 | 1 | 10.0 | 1 | 4.8 |
|  | Yes | 11 | 100.0 | 9 | 90.0 | 20 | 95.2 |
|  | Total | 11 | 100.0 | 10 | 100.0 | 21 | 100.0 |
| Visit 3, Day 8 | No | 10 | 100.0 | 8 | 80.0 | 18 | 90.0 |
|  | Yes | 0 | 0 | 2 | 20.0 | 2 | 10.0 |
|  | Total | 10 | 100.0 | 10 | 100.0 | 20 | 100.0 |

TABLE 16-continued

Individual Amsel's criteria—thin, white, yellow, homogeneous discharge, by visit

| Visit | Thin, white, yellow, homogenous discharge | Once a week n | Once a week % | Twice a week n | Twice a week % | All n | All % |
|---|---|---|---|---|---|---|---|
| Visit 5, Day 15 | No | 7 | 70.0 | 8 | 88.9 | 15 | 78.9 |
|  | Yes | 3 | 30.0 | 1 | 11.1 | 4 | 21.1 |
|  | Total | 10 | 100.0 | 9 | 100.0 | 19 | 100.0 |

Amsel's Criteria—Clue Cells on Microscopy

All patients in the once a week group had no clue cells at visit 3, however clue cells were present for 2 patients at visit 5. In the twice a week group seven patients had no clue cells at visit 3, and 8 patients had no "clue cells" at visit 5.

TABLE 17

Individual Amsel's criteria—clue cells on microscopy, by visit

| Visit | Clue cells on microscopy | Once a week n | Once a week % | Twice a week n | Twice a week % | All n | All % |
|---|---|---|---|---|---|---|---|
| Visit 1, Day 1 | No | 0 | 0 | 2 | 20.0 | 2 | 9.5 |
|  | Yes | 11 | 100.0 | 8 | 80.0 | 19 | 90.5 |
|  | Total | 11 | 100.0 | 10 | 100.0 | 21 | 100.0 |
| Visit 3, Day 8 | No | 10 | 100.0 | 7 | 70.0 | 17 | 85.0 |
|  | Yes | 0 | 0 | 3 | 30.0 | 3 | 15.0 |
|  | Total | 10 | 100.0 | 10 | 100.0 | 20 | 100.0 |
| Visit 5, Day 15 | No | 8 | 80.0 | 8 | 88.9 | 16 | 84.2 |
|  | Yes | 2 | 20.0 | 1 | 11.1 | 3 | 15.8 |
|  | Total | 10 | 100.0 | 9 | 100.0 | 19 | 100.0 |

Amsel's Criteria—Release of a Fishy Odour on Adding Alkali

Nine patients in the once a week group had no fishy odour at visit 3 and at visit 5. In the twice a week group eight patients had no fishy odour at visit 3 and 9 patient had no fishy odour at visit 5.

TABLE 18

Individual Amsel's criteria—release of a fishy odour on adding alkali, by visit

| Visit | Release of a fishy odour on adding alkali | Once a week n | Once a week % | Twice a week n | Twice a week % | All n | All % |
|---|---|---|---|---|---|---|---|
| Visit 1, Day 1 | No | 0 | 0 | 1 | 10.0 | 1 | 4.8 |
|  | Yes | 11 | 100.0 | 9 | 90.0 | 20 | 95.2 |
|  | Total | 11 | 100.0 | 10 | 100.0 | 21 | 100.0 |
| Visit 3, Day 8 | No | 9 | 90.0 | 8 | 80.0 | 17 | 85.0 |
|  | Yes | 1 | 10.0 | 2 | 20.0 | 3 | 15.0 |
|  | Total | 10 | 100.0 | 10 | 100.0 | 20 | 100.0 |
| Visit 5, Day 15 | No | 9 | 90.0 | 9 | 100.0 | 18 | 94.7 |
|  | Yes | 1 | 10.0 | 0 | 0 | 1 | 5.3 |
|  | Total | 10 | 100.0 | 9 | 100.0 | 19 | 100.0 |

Amsel's Criteria—pH of Vaginal Fluid >4.5

Only three patients in the once a week group had a pH of 4.5 or less at visit 3 and only one at visit 5. In the twice a week group there were only three patients that had a pH of 4.5 or less at visit 3, the corresponding figure for visit 5 was 4 patients.

TABLE 19

Individual Amsel's criteria—pH of vaginal fluid >4.5 at according to CRF, by visit

| Visit | pH of vaginal fluid more than 4.5 | Once a week n | Once a week % | Twice a week n | Twice a week % | All n | All % |
|---|---|---|---|---|---|---|---|
| Visit 1, Day 1 | Yes | 11 | 100.0 | 10 | 100.0 | 21 | 100.0 |
|  | Total | 11 | 100.0 | 10 | 100.0 | 21 | 100.0 |
| Visit 3, Day 8 | No | 3 | 30.0 | 3 | 30.0 | 6 | 30.0 |
|  | Yes | 7 | 70.0 | 7 | 70.0 | 14 | 70.0 |
|  | Total | 10 | 100.0 | 10 | 100.0 | 20 | 100.0 |
| Visit 5, Day 15 | No | 1 | 10.0 | 4 | 44.4 | 5 | 26.3 |
|  | Yes | 9 | 90.0 | 5 | 55.6 | 14 | 73.7 |
|  | Total | 10 | 100.0 | 9 | 100.0 | 19 | 100.0 |

Overall Assessment

The overall assessment from the investigator was that 7 patients in both groups received a major, improvement by using the treatment.

TABLE 20

Physicians Overall Assessment

|  | Once a week n | Once a week % | Twice a week n | Twice a week % | All n | All % |
|---|---|---|---|---|---|---|
| Physicians overall assessment |  |  |  |  |  |  |
| No improvement | 2 | 20.0 | 0 | 0 | 2 | 10.5 |
| Slight improvement | 1 | 10.0 | 2 | 22.2 | 3 | 15.8 |
| Major improvement | 7 | 70.0 | 7 | 77.8 | 14 | 73.7 |
| Total | 10 | 100.0 | 9 | 100.0 | 19 | 100.0 | pH Difference

FIG. 7 shows the vaginal pH decrease from Visit 1 (mean value and 95% confidence interval) during treatment once a week (ow) and twice a week (bw) with Laccure vaginal tablet. As seen from the figure on average all patients had a decrease in pH of 0.5 from visit 2 and onwards. From the overall perspective it seems as if the decrease in pH is a much more valuable measure than the pH value itself. Thus, if pH decreases with 0.5 pH-units or more and only one of the other Amsel's criteria is fulfilled, it seems as if the treatment is effective (the treatment is of course also effective if only two or less of the four Amsel criteria are fulfilled). Normally, the decrease of pH should not be lower than to a pH value of 3.5.

Main Effectiveness Conclusions

Data quality of the study, when considering missing data and number of completed patients is good, only 3 patients out of 21 did not complete the study according to protocol.

Three patients out of 10 in the once a week group and 4 patients out of 9 in the twice a week group had a pH value below 4.5 at visit 5 (two weeks). In addition, all patients received a lower pH value compared to visit 1 (day 1), although not always below pH 4.5.

There was a statistical significant decrease in mean pH values from visit 1 to visit 2 (day 3-4) ($p<0.05$), in both treatment groups, and also when combining the two treatment groups.

These results show that there was a decrease in the mean pH over time when using Laccure vaginal tablet. This difference was statistically significant between day 1 and day 3/4 (MV pH—measured in the middle of the vagina).

The overall BV classification according to Amsel's criteria showed that 8 out of 11 (once a week) and 9 out 10 (twice a week) had no BV at the end of the study. The individual Amsel's criteria besides pH level showed that the treatment (both once a week and twice a week) over a 2 week period diminish all BV criteria in almost all of the patients.

Patient's perception on the treatment in the diary clearly showed a complete or partial agreement with the specific questions, i.e. —I have experienced the treatment as user friendly, —I think the duration of the vaginal tablet has been long enough, —The treatment in general has felt good, —I have not experienced the vaginal tablet as messy, —I think the treatment has decreased my problems, —I would consider using this treatment when on market, at day 15 independent of treatment.

The physicians overall assessment showed that patients in most cases had a major improvement by using Laccure vaginal tablets independent of number of tablets (one or two) per week.

Overall Conclusion

The study was well conducted in accordance with ICH GCP with a high number of patients completed the study without missing data.

The pH levels were reduced during the study, which was especially pronounced from visit 1 to visit 2. However, there was no decrease below 4.5 for most patients.

The effect on BV could be established by using the Amsel's criteria independent of treatment group and BV disappeared in almost all patients in both groups already after one week.

Patient overall assessment of using this treatment was very good as was the physician's view of the treatment outcome. All patients considered using the treatment once on the market.

The treatment with Laccure vaginal tablet was considered to be well tolerated within this patient population.

The results of the clinical study Part A were also used to determine the start and design of Part B of the clinical study.

Example 11 pH Regulating Effect and Safety of Laccure Vaginal Tablet in Patients with Bacterial Vaginosis. An Open Controlled Study with Parallel Group and Adaptive Design. Study B Study Objectives
Primary Objective:
To investigate the efficacy of Laccure vaginal tablet in subjects with bacterial vaginosis (BV).
Secondary Objectives:
To investigate the safety, tolerability, pH levels and patient satisfaction of Laccure vaginal tablet in subjects with bacterial vaginosis (BV).
Methodology
The study was of open design with 3 parallel treatment groups. The patients were randomised to either of the following treatments:
Treatment with Laccure vaginal tablet once a week for 1 week (OW).
Treatment with Laccure vaginal tablet twice a week for 1 week (BW).
Control group with no treatment of BV (C).

The patients visited the clinic according to the following schedule:

| Visit 1 | Visit 2 | Visit 3 |
|---|---|---|
| Day 1 | Day 4*) | Day 8 |

*)visit could occur at −1 day

The patients self-administered the device in the evening of Day 1 in the once a week group and in the evening of Day 1 and Day 4 the twice a week group. The patients randomised on Visit 3 self-administered the device in the evening of Day 8 in the once a week group and in the evening of Day 8 and Day 11 the twice a week group.
Number of Subjects
The Full Analysis Set (FAS) and the Per Protocol (PP) were used to present the data. The FAS consisted of all randomised patients who received at least 1 dose of the investigational device (this population was also considered as the safety population). The PP consisted of all randomised patients who received at least 1 dose of the investigational device and who had no major protocol violations, i.e. did not fulfil the inclusion/exclusion criteria, missed visit 3, used antibiotics, had menstruation/bleeding, used wrong number of vaginal tablets and had visit 3 later than day 13. Regarding the control group, the FAS consisted of all patients and the PP of all patients who had no major protocol violations.

| Number of patients | FAS | PP |
|---|---|---|
| Once a week | 37 | 30 |
| Twice a week | 35 | 32 |
| Control | 33 | 28 |
| Total | 105 | 90 |

Diagnosis and Criteria for Inclusion
Women ≥18 years of age with confirmed diagnosis of current bacterial vaginosis, i.e. at least 3 of the following 4 Amsel's criteria present: thin white to yellow homogeneous discharge, clue cells on microscopy, fishy odour when alkali is added, and pH >4.5.
Test Product, Batch No., Dose and Mode of Administration
Laccure vaginal tablet, GMP batch no. 83601-1010-06 and 83601-1010-10, administered in the evening once a week or twice a week for 1 week. At each administration, 1 vaginal tablet was inserted deep into the vagina according to instructions from the investigator.
Duration of Treatment
The treatment period was 1 week.
Reference Treatment
There was no reference treatment. The control group consisted of untreated patients.
Criteria for Evaluation
Primary Endpoint:
To compare the frequency of no BV according to Amsel's criteria at one week between once a week treatment and the untreated control group.
Adverse events reported spontaneously and adverse events upon vulvovaginal examination at the final visit.
Secondary Endpoints:
The frequency of no BV according to Amsel's criteria after one week between the other study groups
Change of vaginal pH over time
Patient satisfaction (user friendliness according to questionnaire at last visit.

Efficacy of the tablet assessed as proportion of patients at one week with each of the individual Amsel's criteria;

Proportion of patients with a thin white to yellow homogeneous discharge

Clue cells on microscopy

Fishy odour when adding alkali pH >4.5.

Safety variables

Statistical Methods

All efficacy variables were analysed using both the FAS and the PP population, when presenting data for Visit 1 (Day 1) to Visit 3 (Day 8).

The primary analysis compared the proportion of subjects with no BV at Visit 3 (Day 8) according to Amsel's criteria between the once a week treatment group and the untreated control group. The response rate was compared between the two groups using Chi-Square test without continuity correction.

The secondary analysis of no BV at Visit 3 (Day 8) according to Amsel's criteria was to compare the treatment twice a week versus the untreated control group and the pooled treatment groups versus the untreated control group. These analyses were performed in the same way as for the primary analysis.

The proportion of subjects with no BV at Visit 3 (Day 8) are presented using frequency tables together with a 95% confidence interval for the proportion of subjects with no BV, by the different treatment groups (i.e. once a week, twice a week, and control group and one for pooled treatment group). The p-values from the Chi-square test will be included in the tables.

The difference between Visit 1 (Day 1) and Visit 2 (Day 4)/Visit 3 (Day 8) in the pH value within each treatment group, (i.e. for the once a week group, twice a week group, pooled treatment groups, and the control group) were analysed using two tests:

1. One-sample t-test and
2. Wilcoxon signed rank test

Subject Questionnaire

The proportion of subjects responding to the different subject satisfaction questions were compared between the once a week group versus the twice a week group using Chi-Square without continuity correction.

Individual Amsel's Criteria:

All the secondary endpoints according to the Amsel's criteria were analysed using Chi-Square without continuity correction.

Results

Bacterial Vaginosis

The number of patients with no BV at visit 3 is presented in Table 21 by analysis set and treatment group. There was a highly statistical significant difference both when comparing the response rates for once a week and twice a week, respectively, to the response rate for the control group (p<0.0001 for all comparisons). This was also true when comparing pooled treatment to the control group (p<0.0001). The results were similar for both FAS and PP. No statistically significant differences between the response rate for treatment once a week versus treatment twice a week could be seen (FAS; p=0.3644, PP; p=0.3013)

TABLE 21

Patients with bacterial vaginosis (BV) according to Amsel's criteria.

| Treatment group | | Visit 1 (Day 1) | | Visit 3 (Day 8) | |
|---|---|---|---|---|---|
| | | FAS | PP | FAS | PP |
| Once a week | total number of patients | 37 | 30 | 34 | 30 |
| | number with no BV | 0 | 0 | 24 | 21 |
| | % with no BV | 0% | 0% | 70.6% | 70.0% |
| Twice a week | total number of patients | 35 | 32 | 35 | 32 |
| | number with no BV | 0 | 0 | 28 | 26 |
| | % with no BV | 0% | 0% | 80.0% | 81.3% |
| Pooled groups (OW + BW) | Total number of patients | 72 | 90 | 69 | 62 |
| | Number with no BV | 0 | 0 | 52 | 47 |
| | % with no BV | 0% | 0% | 75.4% | 75.8% |
| Control | total number of patients | 33 | 28 | 30 | 28 |
| | number with no BV | 0 | 0 | 3 | 3* |
| | % with no BV | 0% | 0% | 10.0% | 10.7%* (correct 7.4%) |

*After database lock it was discovered that one patient in the control group had been randomised to treatment with Laccure Vaginal Tablet already at visit 2 (day 4). This patient should consequently not have been included in the PP analysis set and the correct % of patients with no BV in this group should have been 7.4%.

Individual Amsel's Criteria; Abnormal Discharge, Clue Cells, and Fishy Odour

Tables 22-24 show the number and proportion of patients with abnormal (thin, white to yellow) vaginal discharge, clue cells or fishy odour at baseline (Visit 1) and at one week (Visit 3). pH>4.5.

Number and proportion of patients with thin, white to yellow vaginal discharge is presented in Table 22. There was a statistically significant difference in response rate after one week when comparing once a week, twice a week and pooled treatment to the control group (p<0.0001) both for FAS and PP analysis set. No statistically significant difference was found when comparing once a week with twice a week.

TABLE 22

Number and proportion of patients with a thin white to yellow homogeneous discharge (Amsel's criteria)

| Treatment group | Visit 1 (Day 1) | | Visit 3 (Day 8) | |
|---|---|---|---|---|
| | FAS | PP | FAS | PP |
| Once a week | 94.6% (35/37) | 96.7% (29/30) | 41.2% (14/34) | 43.3% (13/30) |
| Twice a week | 100% (35/35) | 100% (32/32) | 34.3% (12/35) | 31.3% (10/32) |
| Pooled treatment (OW + BW) | 97.2% (70/72) | 98.4% (61/62) | 37.7% (26/69) | 37.1% (23/62) |
| Control | 100% (33/33) | 100% (28/28) | 90% (27/30) | 92.9% (26/28) |

Number and proportion of patients with clue cells on microscopy are presented in Table 23. There was a statistically significant difference in response rate after one week when comparing once a week, twice a week and pooled treatment to the control group (p<0.0001) both for FAS and PP analysis set. No statistically significant difference was found when comparing once a week with twice a week.

TABLE 23

Number and proportion of patients with clue cells on microscopy (Amsel's criteria)

| Treatment group | Visit 1 (Day 1) | | Visit 3 (Day 8) | |
| --- | --- | --- | --- | --- |
| | FAS | PP | FAS | PP |
| Once a week | 94.6% (35/37) | 100% (30/30) | 29.4% (10/34) | 30.0% (9/30) |
| Twice a week | 91.4% (32/35) | 96.9% (31/32) | 14.3% (5/35) | 12.5% (4/32) |
| Pooled treatment (OW + BW) | 93.1% (67/72) | 98.4% (61/62) | 21.7% (15/69) | 21.0% (13/62) |
| Control | 93.9% (31/33) | 96.4% (27/28) | 93.3% (28/30) | 92.9% (26/28) |

Number and proportion of patients with vaginal discharge that releases fishy odour are presented in Table 24. There was a statistically significant difference in response rate after one week when comparing once a week, twice a week and pooled treatment to the control group (p<0.05) both for FAS and PP analysis set. No statistically significant difference was found when comparing once a week with twice a week.

TABLE 24

Number and proportion of patients with vaginal discharge that releases a fishy odour on addition of alkali (Amsel's criteria)

| Treatment group | Visit 1 (Day 1) | | Visit 3 (Day 8) | |
| --- | --- | --- | --- | --- |
| | FAS | PP | FAS | PP |
| Once a week | 91.9% (34/37) | 90.0% (27/30) | 29.4% (10/34) | 26.7% (8/30) |
| Twice a week | 94.3% (33/35) | 93.8% (30/32) | 20.0% (7/35) | 18.8% (6/32) |
| Pooled treatment (OW + BW) | 93.1% (67/72) | 91.9% (57/62) | 24.6% (17/69) | 22.6% (14/62) |
| Control | 81.8% (27/33) | 82.1% (23/28) | 73.3% (22/30) | 71.4% (20/28) |

Change of pH

See FIG. 8.

There was a statistically significant decrease in mean and median pH from baseline (visit 1) to day 4 (visit 2) and to day 8 (visit 3) in the once a week treatment group as well as in the twice a week treatment group in both the FAS and PP analysis sets. The median decrease from baseline to day 4 using one Laccure vaginal tablet was 0.9 pH-unit (p<0.0001), while the pH-decrease was 0.2 pH-units in the control group (p<0.05). The median decrease from baseline to day 8 using Laccure vaginal tablet once or twice a week (pooled treatment) was 0.5 pH-unit (p<0.0001), while the pH-decrease was 0.2 pH-units in the control group (ns). P-values were calculated using the Wilcoxon signed rank test (see FIG. 9).

Number and proportion of patients with vaginal pH>4.5 are presented in Table 25. There was a statistically significant difference in response rate after one week when comparing once a week, twice a week and pooled treatment to the control group (p<0.05) both for FAS and PP analysis set. No statistically significant difference was found when comparing once a week with twice a week.

TABLE 25

Number and proportion of patients with vaginal pH > 4.5 (Amsel's criteria)

| Treatment group | Visit 1 (Day 1) | | Visit 3 (Day 8) | |
| --- | --- | --- | --- | --- |
| | FAS | PP | FAS | PP |
| Once a week | 100% (37/37) | 100% (30/30) | 67.6% (23/34) | 63.3% (19/30) |
| Twice a week | 100% (35/35) | 100% (32/32) | 62.9% (22/35) | 59.4% (19/32) |
| Pooled treatment (OW + BW) | 100% (72/72) | 100% (62/62) | 65.2% (45/69) | 61.3% (38/62) |
| Control | 90.9% (30/33) | 92.9% (26/28) | 90.0% (27/30) | 89.3% (25/28) |

Acceptability/User Friendliness

Patients treated with Laccure vaginal tablet once a week or twice a week for one week completed a questionnaire comprising 9 questions on the last visit day. The response rate and confidence interval for the FAS-analysis set is given in Table 22. The response rates for the PP-analysis were similar and thus not presented in this report.

More than 85% of the patients completely agreed that the treatment is user friendly.

More than 85% of the patients completely agreed that the vaginal tablet is easy to insert.

More than 90% of the patients completely agreed or partly agreed that the vaginal tablet was not messy to use.

More than 90% of the patients completely agreed or partly agreed that it was comfortable not to dose more frequently.

Over 90% of the patients completely agreed or partly agreed that the treatment had been effective and the problem with odour declined.

Safety

There was no Serious Adverse Event (SAE).

Conclusions of the Clinical Study

The study was well conducted according to ICH GCP guidelines with a high number of patients completing the study without missing data. The primary efficacy endpoint to compare the proportion of subjects with no BV according to the Amsel's criteria at Visit 3 (Day 8) between the once a week treatment group versus the untreated control group, was statistically significant in favour for the once a week treatment, both using the FAS and the PP analysis set. The results for the comparisons between twice a week treatment group and the untreated control group, and the pooled treatment group versus the untreated control group were also statistically significant, both when using the FAS and the PP analysis set. No statistical significant differences between the response rates for treatment once a week versus treatment twice a week could be seen.

Comparing the response rate numerically between study A and study B, clearly shows that the effect of treating subjects once a week or twice a week are almost identical.

There was a mean decrease in pH value (MV) from baseline to visit 2 in all three groups. The decrease was statistically significant for all groups. There was also a decrease in pH values from baseline to visit 3, however this decrease was not statistically significant for the control group, only for the two treatment groups. The decrease in pH was substantially larger for the two treatment groups compared to the control group.

In summary subject's perception of using this treatment was very good in terms of efficacy and user friendliness.

The treatment with Laccure vaginal tablet was considered to be well tolerated within this patient population.

The invention claimed is:

1. A composition comprising
   (i) an oligomeric lactic acid component comprising a plurality of oligomeric lactic acids having the following formula

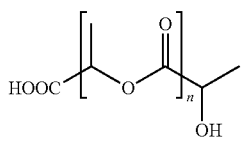

wherein each oligomeric lactic acid has a different value of n, wherein n is an integer from 2 to 20, and
   wherein from about 10% to about 20% w/w of the total weight of the oligomeric lactic acid component is a trimer ($HL_3$) having n equal to 2, the number average molecular weight $M_n$ of the oligomeric lactic acid component is from about 200 to about 500, and the degree of polymerization PDn of the oligomeric lactic acid component is from about 2 to about 3.8, and
   (ii) a mucoadhesive agent, which is hydroxypropyl methylcellulose having a viscosity from 10 to about 20 cP.

2. The composition according to claim 1, wherein the number average molecular weight $M_n$ of the oligomeric lactic acid component is from about 200 to about 400.

3. The composition according to claim 1, wherein the $M_n$ of the oligomeric lactic acid component is from about 230 to about 340.

4. The composition according to claim 1, wherein the polydispersity index of the oligomeric lactic acid component is about 1.45 or more.

5. The composition according to claim 1, wherein the polydispersity index of the oligomeric lactic acid component is from 1.45 to about 6.

6. The composition according to claim 1, wherein the oligomeric lactic acid component comprises a plurality of oligomeric lactic acids, wherein each oligomeric lactic acid has different a value of n, wherein n is an integer from 2 to 18.

7. The composition according to claim 1, wherein the oligomeric lactic acid component has a number average molecular weight in a range of from about 200 to about 240, a weight average molecular weight in a range of from about 290 to about 500, and a polydispersity index in a range of from 1.45 to 2.5.

8. The composition according to claim 7, wherein the oligomeric lactic acid component has a degree of polymerisation of from 2.5 to 3.8.

9. The composition according to claim 1, wherein the oligomeric lactic acid component has a number average molecular weight in a range of from about 255 to about 425, a weight average molecular weight in a range of from about 370 to 580, and a polydispersity index in a range of from 1.45 to 2.5.

10. The composition according to claim 1, wherein the oligomeric lactic acid component comprises:
    from 10 to 20% w/w of $HL_4$ (i.e. n=3)
    from 10 to 15% w/w of $HL_5$ (i.e. n=4)
    from 5 to 15% w/w of $HL_6$ (i.e. n=5).

11. The composition according to claim 1, wherein the oligomeric lactic acid component comprises from 1% to 5% w/w of each of $HL_{10}$, $HL_{11}$, $HL_{12}$, $HL_{13}$, and $HL_{14}$.

12. The composition according to claim 1, wherein the oligomeric lactic acid component has a number average molecular weight of from about 225 to about 275.

13. The composition according to claim 1, formulated for vaginal administration.

14. The composition according to claim 1, in the form of a solid, or semi-solid composition.

15. The composition according to claim 1, in a form selected from the group consisting of a tampon, vagitorium, vaginal aerosol, vaginal cup, vaginal gel, vaginal insert, vaginal patch, vaginal ring, vaginal sponge, vaginal suppository, vaginal cream, vaginal emulsion, vaginal foam, vaginal lotion, vaginal ointment, vaginal powder, vaginal shampoo, vaginal solution, vaginal spray, vaginal suspension, vaginal tablet, vaginal rod, vaginal disc, semipermeable packaging and any combination thereof.

16. The composition according to claim 1, in the form of a vaginal tablet.

17. The composition according to claim 1, further comprising a buffering agent.

18. The composition according to claim 1, further comprising a lyophilisation agent.

19. A method for preparing a lyophilized product comprising a composition as defined in claim 1, the method comprising
    (i) heating a solution comprising water and, optionally, one or more pharmaceutically acceptable excipients, to about 80° C.,
    (ii) adding the mucoadhesive agent in portions and mixing slowly between each addition to obtain a mixture,
    (iii) cooling the mixture to about 55° C.,
    (iv) adding the oligomeric lactic acid component to the mixture with intermittent homogenization to obtain a composition,
    (v) filling the composition into forms,
    (vi) freezing the filled forms at about −25° C., and
    (vii) lyopholizing the frozen filled forms.

20. The composition according to claim 1, wherein the lactic acid component further comprises from 10 to 20% w/w of $HL_2$ (i.e. n=1).

* * * * *